United States Patent
Nakagawa et al.

(10) Patent No.: US 8,946,437 B2
(45) Date of Patent: Feb. 3, 2015

(54) 4-(METHYLAMINOPHENOXY)PYRDIN-3-YL-BENZAMIDE DERIVATIVES FOR TREATING CANCER

(75) Inventors: Takashi Nakagawa, Osaka (JP); Makoto Sakamoto, Osaka (JP); Kazuya Yamaguchi, Osaka (JP); Yuki Terauchi, Osaka (JP); Masamichi Shirakura, Osaka (JP); Yasuo Harada, Osaka (JP); Yutaka Kojima, Osaka (JP); Takumi Sumida, Osaka (JP)

(73) Assignee: Otsuka Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 13/877,276

(22) PCT Filed: Oct. 3, 2011

(86) PCT No.: PCT/JP2011/073165
§ 371 (c)(1),
(2), (4) Date: Jun. 27, 2013

(87) PCT Pub. No.: WO2012/046825
PCT Pub. Date: Apr. 12, 2012

(65) Prior Publication Data
US 2013/0267565 A1  Oct. 10, 2013

Related U.S. Application Data

(60) Provisional application No. 61/389,393, filed on Oct. 4, 2010.

(51) Int. Cl.
| | |
|---|---|
| *A01N 43/40* | (2006.01) |
| *A61K 31/44* | (2006.01) |
| *C07D 211/72* | (2006.01) |
| *C07D 211/84* | (2006.01) |
| *C07D 213/63* | (2006.01) |
| *C07D 213/70* | (2006.01) |
| *C07D 213/72* | (2006.01) |
| *C07D 213/78* | (2006.01) |
| *C07D 213/76* | (2006.01) |
| *C07D 213/75* | (2006.01) |

(52) U.S. Cl.
CPC .......... *C07D 213/76* (2013.01); *C07D 213/75* (2013.01)
USPC .......... 546/297; 546/290; 546/304; 546/312; 514/349; 514/351; 514/352

(58) Field of Classification Search
USPC .......................................... 514/349; 546/297
See application file for complete search history.

(56) References Cited

FOREIGN PATENT DOCUMENTS

| | | |
|---|---|---|
| JP | 2001-089412 | 4/2001 |
| WO | WO 99/24404 A1 | 5/1999 |
| WO | WO 2006/014012 A2 | 2/2006 |
| WO | WO 2007/066784 A2 | 6/2007 |
| WO | WO 2008/044667 A1 | 4/2008 |

OTHER PUBLICATIONS

International Search Report from the European Patent Office for International Application No. PCT/IB2011/073165, mailing date Nov. 23, 2011.

*Primary Examiner* — John Mabry
*Assistant Examiner* — Daniel Carcanague
(74) *Attorney, Agent, or Firm* — Finnegan, Henderson, Farabow, Garrett & Dunner, L.L.P.

(57) ABSTRACT

The present invention provides a novel compound having an excellent antitumor effect, stability and metabolic stability. The compound of the present invention is represented by the following general formula (1) wherein $R^1$ represents a halogen atom, an aryl group, an aryloxy group or a lower alkyl group optionally substituted with one or more halogen atoms; $R^2$ represents hydrogen atom, a halogen atom, a lower alkyl group or a lower alkoxy group; and; m represents an integer of 1 to 3; provided that when m represents 2 or 3, $R^1$s are the same or different.

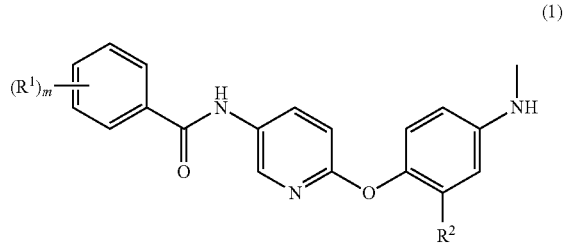

(1)

8 Claims, No Drawings

4-(METHYLAMINOPHENOXY)PYRDIN-3-YL-BENZAMIDE DERIVATIVES FOR TREATING CANCER

CROSS REFERENCE TO RELATED APPLICATIONS

This application is a national phase application based on PCT/JP2011/073165, filed Oct. 3, 2011, which claims the benefit of U.S. Provisional Application No. 61/389,393, filed Oct. 4, 2010; the content of all of which is incorporated herein by reference.

TECHNICAL FIELD

The present invention relates to a heterocyclic compound.

BACKGROUND ART

Since the clinical use of nitrogen mustard as an anticancer agent in the 1940s for the first time in the world, numerous anticancer drugs have ever been developed. Actually, for example, antimetabolites such as 5-fluorouracil, antitumor antibiotics such as adriamycin, platinum complex such as cisplatin, and plant-derived carcinostatics such as vindesine have been subjected to clinical use.

However, most of these carcinostatics have significant side effects such as digestive disorders, myelosuppression and alopecia since they are cytotoxic also to normal cells. Due to the side effects, their range of application is limited, and further, the therapeutic effects themselves are partial and short, in most cases.

In addition to the therapeutic effects and the side effects, metabolic stability is one of important requirements for a drug since pharmacokinetics of a drug in a human body is greatly affected by susceptibility to metabolism. Further, storage stability of a pharmaceutically active ingredient contained in a drug is important for commercial use thereof. Therefore, it is important to evaluate the metabolic stability and the storage stability of a drug candidate.

Developments of new carcinostatics have been made; however, satisfactory results have not yet been obtained. Patent Documents 1, 2 and 3 disclose certain kinds of compounds having fibrosing inhibitory action, antitumor action and STAT3/5 activation inhibitory action, respectively. However, the compounds specifically disclosed in the present application are different from those specifically disclosed in these Patent Documents and it is not known whether the compounds of the present application have antitumor actions.

CITATION LIST

Patent Literature

[Patent Document 1] WO/2006/014012
[Patent Document 2] WO/2007/066784
[Patent Document 3] WO/2008/044667
[Patent Document 4] JP2001-89412

SUMMARY OF INVENTION

Technical Problem

An object of the present invention is therefore to provide a compound which has not only an antitumor effect with less side effects but also metabolic stability and storage stability suitable for a drug.

Solution to Problem

The present inventors intensively conducted studies with the view to attaining the aforementioned object. As a result, they found that a compound represented by the general formula (1) below and a salt thereof have an excellent antitumor effect with less side effects, and metabolic stability and storage stability suitable for a drug. Therefore, they are useful as a medical drug for treating or preventing various cancer types. Examples of the cancer include sex-steroid hormone related cancer (for example, prostate cancer, breast cancer, ovarian cancer, uterine cancer, testicular cancer) and solid cancer (for example, lung cancer, colon cancer, bladder cancer, thyroid cancer, esophageal cancer, liver cancer, brain cancer, pancreatic cancer, gastric cancer, melanoma) and blood cancer (for example, acute lymphoblastic leukemia, chronic lymphocytic leukemia, acute myelogenous leukemia, chronic myelogenous leukemia, multiple myeloma, lymphoma). The term "cancer" in this description includes "tumor". The present invention has been achieved based on the finding.

More specifically, the present invention provides medicinal drugs shown in item 1.

Item 1: A compound represented by the following general formula (1) or a salt thereof:

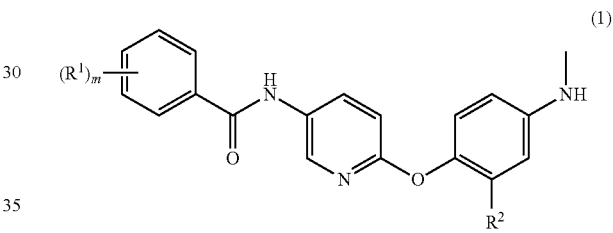

wherein $R^1$ represents a halogen atom, an aryl group, an aryloxy group or a lower alkyl group optionally substituted with one or more halogen atoms;
$R^2$ represents a hydrogen atom, a halogen atom, a lower alkyl group or a lower alkoxy group; and
m represents an integer of 1 to 3;
provided that when m represents 2 or 3, $R^1$s are the same or different.

Item 2: The compound according to Item 1 or a salt thereof, wherein $R^2$ represents a hydrogen atom.
Item 3: The compound according to Item 1 or a salt thereof, wherein $R^2$ represents a halogen atom.
Item 4: The compound according to Item 1 or a salt thereof, wherein $R^2$ represents a lower alkyl group.
Item 5: The compound according to Item 1 or a salt thereof, wherein $R^2$ represents a lower alkoxy group.
Item 6: The compound according to Item 1 or a salt thereof, which is selected from the group consisting of:
N-{6-[2-fluoro-4-(methylamino)phenoxy]pyridin-3-yl}-4-phenoxybenzamide,
N-{6-[2-fluoro-4-(methylamino)phenoxy]pyridin-3-yl}biphenyl-4-carboxamide,
N-{6-[2-fluoro-4-(methylamino)phenoxy]pyridin-3-yl}-4-(trifluoromethyl)benzamide,
2-fluoro-N-{6-[2-fluoro-4-(methylamino)phenoxy]pyridin-3-yl}-4-(trifluoromethyl)benzamide,
2,3,4-trifluoro-N-{6-[2-fluoro-4-(methylamino)phenoxy]pyridin-3-yl}benzamide,
N-{6-[2-methyl-4-(methylamino)phenoxy]pyridin-3-yl}-4-phenoxybenzamide, N-{6-[2-methyl-4-(methylamino)phenoxy]pyridin-3-yl}biphenyl-4-carboxamide,
N-{6-[2-methyl-4-(methylamino)phenoxy]pyridin-3-yl}-4-(trifluoromethyl)benzamide,
2-fluoro-N-{6-[2-methyl-4-(methylamino)phenoxy]pyridin-3-yl}-4-(trifluoromethyl)benzamide,
N-{6-[4-(methylamino)phenoxy]pyridin-3-yl}-4-phenoxybenzamide,
N-{6-[4-(methylamino)phenoxy]pyridin-3-yl}biphenyl-4-carboxamide,
N-{6-[2-methoxy-4-(methylamino)phenoxy]pyridin-3-yl}-4-(trifluoromethyl)benzamide,
N-{6-[2-methoxy-4-(methylamino)phenoxy]pyridin-3-yl}-4-phenoxybenzamide,
N-{6-[2-methoxy-4-(methylamino)phenoxy]pyridin-3-yl}biphenyl-4-carboxamide,
2-fluoro-N-{6-[2-methoxy-4-(methylamino)phenoxy]pyridin-3-yl}-4-(trifluoromethyl)benzamide,
2,3,4-trifluoro-N-{6-[2-methoxy-4-(methylamino)phenoxy]pyridin-3-yl}benzamide,
2,3,4-trifluoro-N-{6-[2-methyl-4-(methylamino)phenoxy]pyridin-3-yl}benzamide,
N-{6-[4-(methylamino)phenoxy]pyridin-3-yl}-4-(trifluoromethyl)benzamide,
2-fluoro-N-{6-[4-(methylamino)phenoxy]pyridin-3-yl}-4-(trifluoromethyl)benzamide, and
2,3,4-trifluoro-N-{6-[4-(methylamino)phenoxy]pyridin-3-yl}benzamide.

Item 7: The compound according to Item 1, which is selected from the group consisting of:
N-{6-[2-fluoro-4-(methylamino)phenoxy]pyridin-3-yl}-4-phenoxybenzamide,
N-{6-[2-fluoro-4-(methylamino)phenoxy]pyridin-3-yl}biphenyl-4-carboxamide,
N-{6-[2-fluoro-4-(methylamino)phenoxy]pyridin-3-yl}-4-(trifluoromethyl)benzamide,
2-fluoro-N-{6-[2-fluoro-4-(methylamino)phenoxy]pyridin-3-yl}-4-(trifluoromethyl)benzamide,
2,3,4-trifluoro-N-{6-[2-fluoro-4-(methylamino)phenoxy]pyridin-3-yl}benzamide,
N-{6-[2-methyl-4-(methylamino)phenoxy]pyridin-3-yl}-4-phenoxybenzamide,
N-{6-[2-methyl-4-(methylamino)phenoxy]pyridin-3-yl}biphenyl-4-carboxamide,
N-{6-[2-methyl-4-(methylamino)phenoxy]pyridin-3-yl}-4-(trifluoromethyl)benzamide,
2-fluoro-N-{6-[2-methyl-4-(methylamino)phenoxy]pyridin-3-yl}-4-(trifluoromethyl)benzamide,
N-{6-[4-(methylamino)phenoxy]pyridin-3-yl}-4-phenoxybenzamide,
N-{6-[4-(methylamino)phenoxy]pyridin-3-yl}biphenyl-4-carboxamide,
N-{6-[2-methoxy-4-(methylamino)phenoxy]pyridin-3-yl}-4-(trifluoromethyl)benzamide,
N-{6-[2-methoxy-4-(methylamino)phenoxy]pyridin-3-yl}-4-phenoxybenzamide,
N-{6-[2-methoxy-4-(methylamino)phenoxy]pyridin-3-yl}biphenyl-4-carboxamide,
2-fluoro-N-{6-[2-methoxy-4-(methylamino)phenoxy]pyridin-3-yl}-4-(trifluoromethyl)benzamide,
2,3,4-trifluoro-N-{6-[2-methoxy-4-(methylamino)phenoxy]pyridin-3-yl}benzamide,
2,3,4-trifluoro-N-{6-[2-methyl-4-(methylamino)phenoxy]pyridin-3-yl}benzamide,
N-{6-[4-(methylamino)phenoxy]pyridin-3-yl}-4-(trifluoromethyl)benzamide,
2-fluoro-N-{6-[4-(methylamino)phenoxy]pyridin-3-yl}-4-(trifluoromethyl)benzamide,
2,3,4-trifluoro-N-{6-[4-(methylamino)phenoxy]pyridin-3-yl}benzamide,
N-{6-[2-fluoro-4-(methylamino)phenoxy]pyridin-3-yl}-4-phenoxybenzamide hydrochloride,
2-fluoro-N-{6-[2-fluoro-4-(methylamino)phenoxy]pyridin-3-yl}-4-(trifluoromethyl)benzamide hydrochloride,
2,3,4-trifluoro-N-{6-[2-fluoro-4-(methylamino)phenoxy]pyridin-3-yl}benzamide hydrochloride,
N-{6-[2-methyl-4-(methylamino)phenoxy]pyridin-3-yl}-4-(trifluoromethyl)benzamide hydrochloride,
2,3,4-trifluoro-N-{6-[2-methyl-4-(methylamino)phenoxy]pyridin-3-yl}benzamide hydrochloride,
N-{6-[2-methoxy-4-(methylamino)phenoxy]pyridin-3-yl}-4-phenoxybenzamide hydrochloride,
N-{6-[2-methoxy-4-(methylamino)phenoxy]pyridin-3-yl}-4-(trifluoromethyl)benzamide hydrochloride,
2-fluoro-N-{6-[2-methoxy-4-(methylamino)phenoxy]pyridin-3-yl}-4-(trifluoromethyl)benzamide hydrochloride,
2,3,4-trifluoro-N-{6-[2-methoxy-4-(methylamino)phenoxy]pyridin-3-yl}benzamide hydrochloride,
N-{6-[4-(methylamino)phenoxy]pyridin-3-yl}-4-(trifluoromethyl)benzamide hydrochloride,
2-fluoro-N-{6-[4-(methylamino)phenoxy]pyridin-3-yl}-4-(trifluoromethyl)benzamide hydrochloride, and
2,3,4-trifluoro-N-{6-[4-(methylamino)phenoxy]pyridin-3-yl}benzamide hydrochloride.

Item 8: A pharmaceutical composition comprising a compound represented by the general formula (1) or a salt thereof according to any one of Items 1 to 7, and a pharmacologically acceptable carrier.

Item 9: A pharmaceutical composition according to Item 8 for preventing and/or treating cancer.

Item 10: A compound represented by the general formula (1) or a salt thereof according to any one of Items 1 to 7 for use in the pharmaceutical composition.

Item 11: Use of a compound represented by the general formula (1) or a salt thereof according to any one of Items 1 to 7 as a pharmaceutical composition.

Item 12: Use of a compound represented by the general formula (1) or a salt thereof according to any one of Items 1 to 7 for the production of a pharmaceutical composition.

Item 13: A method of preventing and/or treating cancer, comprising administering to a patient in need thereof a compound represented by the general formula (1) or a salt thereof according to any one of Items 1 to 7.

DESCRIPTION OF EMBODIMENTS

Specific examples of individual groups shown in the general formula (1) are as follows.

Examples of the lower alkoxy group include linear or branched alkoxy groups having 1 to 6 carbon atoms such as methoxy, ethoxy, propoxy, isopropoxy, butoxy, tert-butoxy, pentyloxy, and hexyloxy groups.

Examples of the lower alkyl group include linear or branched alkyl groups having 1 to 6 carbon atoms such as methyl, ethyl, propyl, isopropyl, 2,2-dimethylpropyl, 1-ethylpropyl, butyl, isobutyl, tert-butyl, isopentyl, pentyl, and hexyl groups.

Examples of the lower alkyl group optionally substituted with one or more halogen atoms include, in addition to the above described lower alkyl groups, linear or branched alkyl groups having 1 to 6 carbon atoms which may be substituted by 1 to 3 halogen atoms such as trifluoromethyl, trichloromethyl, chloromethyl, bromomethyl, fluoromethyl, iodomethyl, difluoromethyl, dibromomethyl, dichloromethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, and 5,6-dibromohexyl groups.

Examples of the halogen atom include a fluorine atom, chlorine atom, bromine atom and iodine atom.

Examples of the aryl group include $C_6$ to $C_{10}$ aromatic groups such as phenyl, 1-naphthyl, 2-naphthyl, o-tolyl, m-tolyl and p-tolyl groups.

Examples of the aryloxy group include $C_6$ to $C_{10}$ aryloxy groups such as phenoxy, 1-naphthyloxy and 2-naphthyloxy.

One preferred example is a compound represented by the general formula (1) or a salt thereof, wherein $R^1$ represents an aryl group, an aryloxy group or a lower alkyl group optionally substituted with one or more halogen atoms;

$R^2$ represents a hydrogen atom, a halogen atom, a lower alkyl group or a lower alkoxy group; and m represents an integer of 1.

Another preferred example is a compound represented by the general formula (1) or a salt thereof, wherein $R^1$ represents a halogen atom;

$R^2$ represents a hydrogen atom, a halogen atom, a lower alkyl group or a lower alkoxy group; and m represents an integer of 1 to 3;
provided that when m represents 2 or 3, $R^1$s are the same or different.

Further another preferred example is a compound represented by the general formula (1) or a salt thereof, wherein $R^1$ represents a halogen or a lower alkyl group optionally substituted with one or more halogen atoms;

$R^2$ represents a hydrogen atom, a halogen atom, a lower alkyl group or a lower alkoxy group; and m represents an integer of 2;
provided that $R^1$s are the same or different.

Table 1 lists abbreviations used throughout the specification.

TABLE 1

| List of Abbreviation | |
|---|---|
| Abbreviation | Description |
| AcOEt | ethyl acetate |
| AcONa | sodium acetate |
| BINAP | 2,2'-bis(diphenylphosphino)-1,1'-binaphthyl |
| AcOH | acetic acid |
| mCPBA | m-chloroperoxybenzoic acid |
| conc. | concentrated |
| DABCO | 1,4-diazabicyclo[2.2.2]octane |
| DBN | 1,5-diazabicyclo[4.3.0]non-5-ene |
| DBU | 1,8-diazabicyclo[5.4.0]undec-7-ene |
| DEAD | diethyl azodicarboxylate |
| DEPC | diethyl cyanophosphonate |
| DIBAH | diisobutylaluminium hydride |
| DIPEA | N,N-diisopropylethylamine |
| DMA | dimethylacetamide |
| DMAP | 4-(N,N-dimethylamino)pyridine |
| DMF | N,N-dimethylformamide |
| DMSO | dimethyl sulfoxide |
| dec. | decomposition |
| $Et_2O$ | diethyl ether |
| $Et_3N$ | triethylamine |
| EtOH | ethyl alcohol |
| HOAT | 1-hydroxy-7-azabenzotriazole |
| HOBT | 1-hydroxybenzotriazole |
| HOBT-$H_2O$ | 1-hydroxybenzotriazole hydrate |
| MeOH | methyl alcohol |
| mp | melting point |
| MsCl | methanesulfonyl chloride |

TABLE 1-continued

| List of Abbreviation | |
|---|---|
| Abbreviation | Description |
| SRB | sulforhodamine B |
| TCA | trichloroacetic acid |
| $NaBH(OAc)_3$ | sodium triacetoxyborohydride |
| n-BuLi | n-butyllithium |
| NMP | N-methylpyrrolidone |
| $Pd(OAc)_2$ | palladium(II) acetate |
| $Pd(PPh_3)_4$ | tetrakis(triphenylphosphine)palladium(0) |
| Pd/C | palladium on carbon |
| $Pd_2(dba)_3$ | tris(dibenzylideneacetone)dipalladium(0) |
| $PPh_3$ | triphenylphosphine |
| PPTS | pyridinium p-toluenesulfonate |
| OD | optical density |
| Pt/C | platinum on carbon |
| TBAF | tetra-n-butylammonium fluoride |
| TBDMSCl | tert-butyldimethylsilyl chloride |
| TFA | trifluoroacetic acid |
| THF | tetrahydrofuran |
| TMEDA | tetramethylethylenediamine |
| TMPDA | tetramethylpropylenediamine |
| WSC | 1-(3-dimethylaminopropyl)-3-ethylcarbodiimide |
| WSC-HCl | 1-(3-dimethylaminopropyl)-3-ethylcarbodiimide hydrochloride |

Methods for producing compounds according to the present invention will be described below.

The heterocyclic compound of the present invention represented by the general formula (1) or its salt can be readily produced by persons skilled in the art using technical knowledge, based on the Examples and Reference Examples of the present specification. For example, the heterocyclic compound or its salt can be produced according to the processes shown in the following reaction formulae.

[Reaction Formula 1]

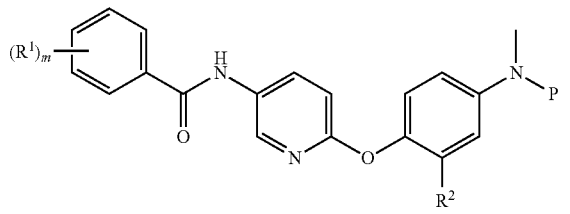

(2)

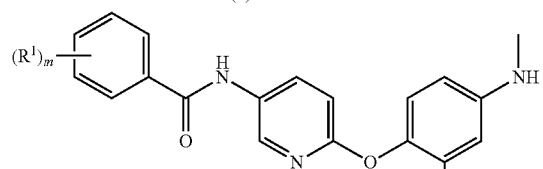

(1)

wherein $R^1$, $R^2$, and m are the same as above, and P is an amino-protecting group.

Compound (1) can be produced by subjecting Compound (2) to deprotection. While the conditions for the deprotection vary depending on the kinds of the amino-protecting group P, it is not particularly limited insofar as the deprotection proceeds. For example, the deprotection can be performed according to a method described in T. W. Green, Protective Groups in Organic Synthesis, 4th edition, John Wiley & Sons, Inc., p696-926).

When P is tert-butoxycarbonyl, the deprotection can be performed in an inert solvent in the presence of 1.0 to 100.0 moles of an acid per mole of Compound (2).

Examples of the acid include inorganic acids such as hydrochloric acid and sulfuric acid; and organic acids such as TFA and methanesulfonic acid.

The solvent used is not particularly limited insofar as it does not inhibit the reaction and allows the starting material to be dissolved therein to a certain extent. Preferable examples thereof include AcOEt, MeOH, EtOH, 1,4-dioxane, methylene chloride, chloroform, isopropanol, DMF and NMP.

The reaction is typically performed at a temperature of −10 to 100° C., preferably 0 to 50° C., and is typically completed in 0.5 to 50 hours, preferably 1 to 20 hours.

Reaction Formulae A to C for preparation of the starting compound (2) is explained in detail in the following.

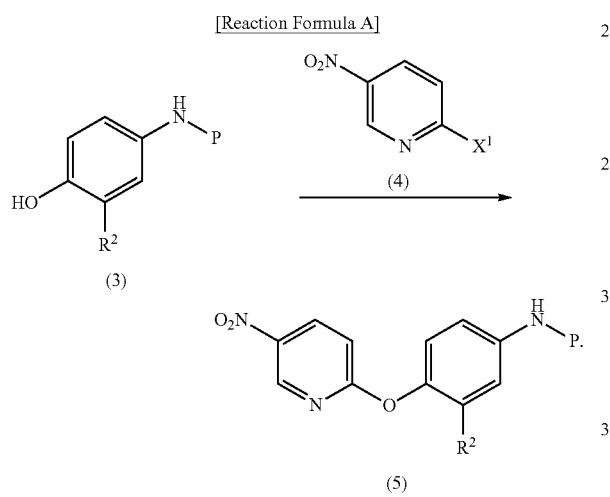

wherein $R^2$ and P are the same as above, and $X^1$ is a leaving group.

Compound (5) can also be produced by reacting Compound (3) with Compound (4). The reaction can be performed in the presence or absence of a base, in an inert solvent or without any solvent.

Examples of the leaving group represented by $X^1$ include halogen (e.g., fluorine, chlorine, bromine, iodine), optionally halogenated C1-6 alkylsulfonyloxy (e.g., methanesulfonyloxy, ethanesulfonyloxy, trichloromethanesulfonyloxy, trifluoromethanesulfonyloxy, etc.), arylsulfonyloxy (e.g., C6-10 arylsulfonyloxy (e.g., phenylsulfonyloxy, naphthylsulfonyloxy) optionally substituted by 1 to 3 substituents selected from the group of C1-6 alkyl group (e.g., methyl, ethyl, etc.), C1-6 alkoxy (e.g., methoxy, ethoxy, etc.) and a nitro group), haloacyloxy (e.g., trichloroacetoxy, trifluoroacetoxy and the like), and the like. Specific examples include phenylsulfonyloxy, m-nitrophenylsulfonyloxy, p-toluenesulfonyloxy, trichloroacetoxy, trifluoroacetoxy and the like.

Examples of the inert solvent include water; ethers such as dioxane, THF, $Et_2O$, diethylene glycol dimethyl ether and ethylene glycol dimethyl ether; aromatic hydrocarbons such as benzene, toluene and xylene; halogenated hydrocarbons such as dichloromethane, dichloroethane, chloroform and carbon tetrachloride; lower (C1-6) alcohols such as MeOH, EtOH and isopropanol; ketones such as acetone and methyl ethyl ketone; polar solvents such as DMF, DMSO, hexamethylphosphoric triamide and acetonitrile; and mixtures thereof.

A wide variety of known bases can be used as the base. Examples of the base include inorganic bases, for example, alkali metal hydroxides such as sodium hydroxide, potassium hydroxide, cesium hydroxide and lithium hydroxide; alkali metal carbonates such as sodium carbonate, potassium carbonate, cesium carbonate, lithium carbonate, lithium hydrogencarbonate, sodium hydrogencarbonate and potassium hydrogencarbonate; alkali metals such as sodium and potassium; metal amides such as sodium amide; metal hydrides such as sodium hydride, and potassium hydride; alkali metal alkoxides such as sodium methoxide, sodium ethoxide, potassium methoxide and potassium ethoxide; and organic bases, for example, $Et_3N$; DIPEA; tripropylamine; pyridine; quinoline; DBN; DBU; and DABCO. These bases can be used alone or in a combination of two or more.

The above reaction may be performed by adding to the reaction system, as required, an alkali metal iodide serving as a reaction accelerator, such as potassium iodide or sodium iodide.

Compound (4) is typically used in an amount of at least 0.5 mole, preferably 1 to 5 moles, per mole of Compound (3).

The base is typically used in an amount of 0.5 to 10 moles, preferably 1 to 6 moles, per mole of Compound (3).

The reaction is typically performed at a temperature of 0 to 250° C., preferably 0 to 200° C., and is typically completed in 1 to 80 hours.

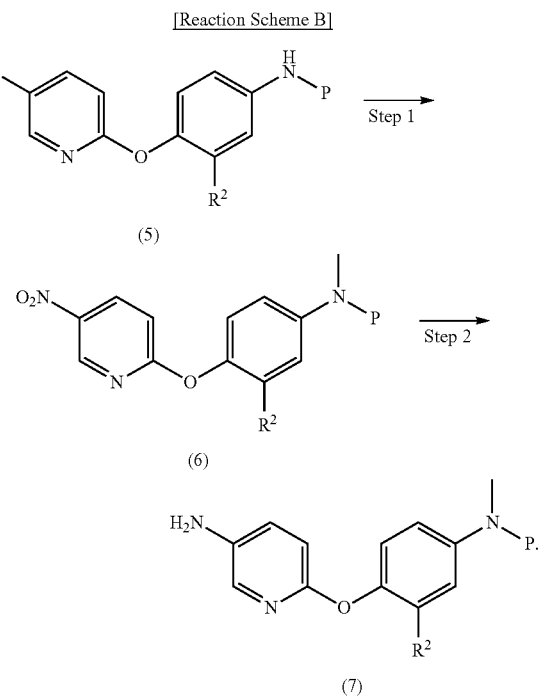

wherein $R^2$ and P are the same as above.

Step 1

Compound (6) can be produced by reacting Compound (5) with a methylating reagent. The reaction can be performed in the presence or absence of a base, in an inert solvent or without any solvent.

Examples of the methylating reagent include iodomethane, dimethyl sulfate, dimethyl carbonate, methyl trifluoromethanesulfonate, methylfluorosulfonate, and the like.

Examples of the inert solvent include water; ethers such as dioxane, THF, $Et_2O$, diethylene glycol dimethyl ether and ethylene glycol dimethyl ether; aromatic hydrocarbons such as benzene, toluene and xylene; halogenated hydrocarbons such as dichloromethane, dichloroethane, chloroform and carbon tetrachloride; lower (C1-6) alcohols such as MeOH, EtOH and isopropanol; ketones such as acetone and methyl ethyl ketone; polar solvents such as DMF, DMSO, hexamethylphosphoric triamide and acetonitrile; and mixtures thereof.

A wide variety of known bases can be used as the base. Examples of the base include inorganic bases, for example, alkali metal hydroxides such as sodium hydroxide, potassium hydroxide, cesium hydroxide and lithium hydroxide; alkali metal carbonates such as sodium carbonate, potassium carbonate, cesium carbonate, lithium carbonate, lithium hydrogencarbonate, sodium hydrogencarbonate and potassium hydrogencarbonate; alkali metals such as sodium and potassium; metal amides such as sodium amide; metal hydrides such as sodium hydride, and potassium hydride; alkali metal alkoxides such as sodium methoxide, sodium ethoxide, potassium methoxide and potassium ethoxide; and organic bases, for example, $Et_3N$; DIPEA; tripropylamine; pyridine; quinoline; DBN; DBU; and DABCO. These bases can be used alone or in a combination of two or more.

The methylating agent is typically used in an amount of 0.9 to 10 moles, preferably 1 to 5 moles, per mole of Compound (5).

The base is typically used in an amount of 0.5 to 10 moles, preferably 1 to 5 moles, per mole of Compound (5).

The reaction is typically performed at a temperature of −10° C. to 100° C., preferably 0° C. to 80° C., and is typically completed in 0.5 to 48 hours, preferably 1 to 24 hours.

Step 2

Compound (7) can be produced by reducing Compound (6). The reduction can be performed in the presence of a catalytic hydrogenation reducing agent, in an inert solvent.

Examples of the catalytic hydrogenation reducing agent include palladium black, palladium carbon, platinum oxide, platinum black and Raney nickel.

Examples of the inert solvent include carboxylic acids such as formic acid and acetic acid; ethers such as dioxane, THF, $Et_2O$, diethylene glycol dimethyl ether, and ethylene glycol dimethyl ether; esters such as methyl acetate, AcOEt and isopropyl acetate; and lower (e.g., C1-6) alcohols such as MeOH, EtOH and isopropanol.

The reaction can be typically performed in a hydrogen atmosphere at atmospheric pressure to about 20 atm, and preferably atmospheric pressure to 10 atm; or in the presence of a hydrogen donor such as formic acid, ammonium formate, cyclohexene, or hydrazine hydrate.

The catalytic hydrogenation reducing agent is typically used in the amount of 0.1 to 40 wt %, and preferably 1 to 20 wt %, based on Compound (6).

The reaction is typically performed at a temperature of −30 to 100° C., and preferably 0° C. to 60° C.

[Reaction Formula C]

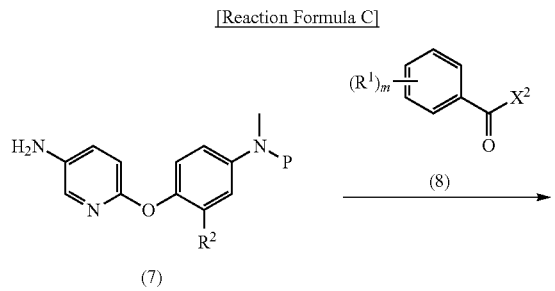

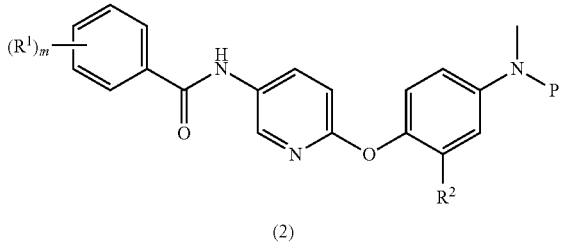

wherein $R^1$, $R^2$, m and P are the same as above, and $X^2$ is a leaving group such as a halogen atom (fluorine, chlorine, bromine and iodine) and hydroxy.

Compound (2) can be produced by reacting Compound (7) with Compound (8).

When $X^2$ is a halogen atom, the reaction can be performed in the presence or absence of a base, in an inert solvent.

Examples of the inert solvent include water; ethers such as dioxane, THF, $Et_2O$, diethylene glycol dimethyl ether and ethylene glycol dimethyl ether; esters such as methyl acetate, AcOEt and isopropyl acetate; aromatic hydrocarbons such as benzene, toluene and xylene; halogenated hydrocarbons such as dichloromethane, dichloroethane, chloroform and carbon tetrachloride; lower (C1-6) alcohols such as MeOH, EtOH and isopropanol; ketones such as acetone and methyl ethyl ketone; polar solvents such as DMF, DMSO, hexamethylphosphoric triamide and acetonitrile; and mixtures thereof.

A wide variety of known bases can be used as the base. Examples of the base include inorganic bases, for example, alkali metal hydroxides such as sodium hydroxide, potassium hydroxide, cesium hydroxide and lithium hydroxide; alkali metal carbonates such as sodium carbonate, potassium carbonate, cesium carbonate, lithium carbonate, lithium hydrogencarbonate, sodium hydrogencarbonate and potassium hydrogencarbonate; alkali metals such as sodium and potassium; metal amides such as sodium amide; metal hydrides such as sodium hydride, and potassium hydride; alkali metal alkoxides such as sodium methoxide, sodium ethoxide, potassium methoxide and potassium ethoxide; and organic bases, for example, $Et_3N$; DIPEA; tripropylamine; pyridine; quinoline; DBN; DBU; and DABCO. These bases can be used alone or in a combination of two or more.

In this reaction, compound (8) is typically used in an amount of at least 0.5 mole, preferably 1 to 5 moles, per mole of compound (7).

The base is typically used in an amount of 0.5 to 10 moles, preferably 1 to 5 moles, per mole of Compound (5).

The reaction is typically performed at a temperature of −10° C. to 100° C., preferably 0° C. to 80° C., and is typically completed in 5 minutes to 48 hours, preferably 0.5 to 24 hours.

When $X^2$ is hydroxy, Compound (2) can be produced by reacting Compound (7) with Compound (8) according to a known amide bond formation reaction. Conditions for known amide bond formation reactions can be easily employed in this amide formation reaction. For example, the following reaction methods can be employed: (i) a mixed acid anhydride method, in which Compound (8) is reacted with an alkyl haloformate to form a mixed acid anhydride, and then the mixed acid anhydride is reacted with Compound (7); (ii) an active ester method, in which Compound (8) is converted to an activated ester such as a phenyl ester, p-nitrophenyl ester, N-hydroxysuccinimide ester, or 1-hydroxybenzotriazole ester, or to an activated amide with benzoxazoline-2-thione, and then the activated ester or amide is reacted with Compound (7); (iii) a using activating agent, in which Compound (7) is subjected to a condensation reaction with Compound (8) in the presence of an activating agent; and (iv) other methods, for example, a method in which Compound (8) is converted to a carboxylic anhydride using a dehydrating agent such as acetic anhydride, and then the carboxylic anhydride is reacted with Compound (7), a method in which an ester of Compound (8) with a C1-6 alcohol is reacted with Compound (7) at a high pressure and a high temperature, and a method in which an acid halide of Compound (8), i.e., a carboxylic acid halide, is reacted with Compound (7).

Generally, the mixed acid anhydride method (i) can be performed in the presence or absence of a base, in an inert solvent.

Examples of the inert solvent include halogenated hydrocarbons such as chloroform, dichloromethane, dichloroethane and carbon tetrachloride; aromatic hydrocarbons such as benzene, toluene and xylene; ethers such as $Et_2O$, diisopropyl ether, THF and dimethoxyethane; esters such as methyl acetate, AcOEt and isopropyl acetate; aprotic polar solvents such as DMF, dimethylsulfoxide and hexamethylphosphoric triamide; and mixtures thereof.

Examples of the base include organic bases such as $Et_3N$, trimethylamine, pyridine, dimethylaniline, DIPEA, dimethylaminopyridine, N-methylmorpholine, DBN, DBU and DABCO; inorganic bases, for example, carbonates such as sodium carbonate, potassium carbonate, sodium hydrogencarbonate and potassium hydrogencarbonate; metal hydroxides such as sodium hydroxide, potassium hydroxide and calcium hydroxide; metal hydrides such as potassium hydride and sodium hydride; metals such as potassium and sodium; metal amides such as sodium amide; and metal alkoxides such as sodium methoxide and sodium ethoxide.

Examples of the alkyl haloformate usable in the mixed acid anhydride method include methyl chloroformate, methyl bromoformate, ethyl chloroformate, ethyl bromoformate and isobutyl chloroformate. In this method, Compound (7), an alkyl haloformate, and Compound (8) are preferably used in equimolar amounts, but each of the alkyl haloformate and Compound (8) can also be used in an amount of 0.5 to 2 moles per mole of Compound (7).

The reaction is typically performed at −20 to 150° C., preferably at 10 to 50° C., typically completed in 5 minutes to 30 hours, preferably for 10 minutes to 25 hours.

The method (iii), in which a condensation reaction is performed in the presence of an activating agent, can be performed in an inert solvent in the presence or absence of a base.

Examples of the inert solvent include halogenated hydrocarbons such as chloroform, dichloromethane, dichloroethane and carbon tetrachloride; aromatic hydrocarbons such as benzene, toluene and xylene; ethers such as $Et_2O$, diisopropyl ether, THF and dimethoxyethane; esters such as methyl acetate, AcOEt and isopropyl acetate; aprotic polar solvents such as DMF, dimethylsulfoxide and hexamethylphosphoric triamide; and mixtures thereof.

Examples of the base include organic bases such as $Et_3N$, DIPEA, trimethylamine, pyridine, dimethylaniline, N-ethyldiisopropylamine, dimethylaminopyridine, N-methylmorpholine, DBN, DBU, and DABCO; inorganic bases, for example, carbonates such as sodium carbonate, potassium carbonate, sodium hydrogencarbonate and potassium hydrogencarbonate; metal hydroxides such as sodium hydroxide, potassium hydroxide and calcium hydroxide; metal hydrides such as potassium hydride and sodium hydride; metals such as potassium and sodium; metal amides such as sodium amide; and metal alkoxides such as sodium methoxide and sodium ethoxide.

Examples of the activating agent include dicyclohexylcarbodiimide, WSC, DEPC, DMT-MM, triphenylphosphine, diphenylphosphinyl chloride, phenyl-N-phenylphosphoramide chloridate, diethyl chlorophosphate, diethyl cyanophosphate, diphenylphosphoric azide and bis(2-oxo-3-oxazolidinyl)phosphinic chloride and carbonyldiimidazole. A suitable amount of the activating agent is typically at least 0.9 mole, preferably 1 to 5 moles per mole of Compound (8).

An additive can be used together with the activating agent. Examples of the additive include HOAT, HOBT, and the like.

The reaction is typically performed at −20 to 180° C., preferably at 0 to 150° C., and is typically completed in 5 minutes to 90 hours.

When the method in which an acid halide of Compound (7) is reacted with Compound (8), which is mentioned above as one of the other methods (iv), is employed, the reaction can be performed in the presence of a base, in an inert solvent. Examples of the base include a wide variety of known bases, such as those similar to bases usable for the mixed acid anhydride method (i). In addition to the above-mentioned be solvents, Examples of the inert solvent include alcohols such as methanol, ethanol, isopropanol, propanol, butanol, 3-methoxy-1-butanol, ethyl cellosolve and methyl cellosolve; acetonitrile; pyridine; acetone; and water. The ratio of Compound (7) to the acid halide of Compound (8) is not limited, and can be suitably selected from a wide range. It is typically suitable to use, for example, at least 0.9 mole, preferably 1 to 5 moles of Compound (7), per mole of the acid halide of Compound (8).

The reaction is typically performed at −20 to 180° C., preferably at 0 to 150° C., and is typically completed in 5 minutes to 30 hours.

The starting compounds and intermediate compounds shown in each of the above-mentioned reaction formulas can be subjected, where necessary before being applied to reactions, to protection of a functional group with a suitable protecting group by a known method, and to deprotection of the protecting group by a known method after completion of the reaction.

In addition, compounds in the form in which a solvate (for example, a hydrate, ethanolate, etc.) was added to the starting material compounds and object compounds shown in each of the reaction formulae are included in each of the formulae.

The compound (1) according to the present invention includes stereoisomers and optical isomers.

The starting material compounds and object compounds represented by each of the reaction formulae can be used in an appropriate salt form. The object compounds obtained in each step can be used in the next step without being isolated.

Each of the object compounds obtained according to the above reaction formulae can be isolated and purified from the reaction mixture by, for example, after cooling the reaction mixture, performing an isolation procedure such as filtration, concentration, extraction, etc., to separate a crude reaction product, and then subjecting the crude reaction product to a general purification procedure such as column chromatography, recrystallization, etc.

Among the compounds of the present invention, those having a basic group can easily form salts with common pharmaceutically acceptable acids. Examples of such acids include hydrochloric acid, hydrobromic acid, nitric acid, sulfuric acid, phosphoric acid and other inorganic acids, methansulfonic acid, p-toluenesulfonic acid, acetic acid, citric acid, tartaric acid, maleic acid, fumaric acid, malic acid, lactic acid and other organic acids, etc.

Among the compounds of the present invention, those having an acidic group can easily form salts by reacting with pharmaceutically acceptable basic compounds. Examples of such basic compounds include sodium hydroxide, potassium hydroxide, calcium hydroxide, sodium carbonate, potassium carbonate, sodium hydrogencarbonate, potassium hydrogencarbonate, etc.

In the compound of the present invention, one or more atoms can be substituted with one or more isotopic atoms. Examples of the isotopic atoms include deuterium ($^2$H), tritium ($^3$H), $^{13}$C, $^{14}$N, $^{18}$O, etc.

The following is an explanation of pharmaceutical preparations comprising the compound of the present invention as an active ingredient.

Such pharmaceutical preparations are obtained by formulating the compound of the present invention into usual pharmaceutical preparations, using usually employed diluents or excipients such as fillers, extenders, binders, wetting agents, disintegrants, surfactants, lubricants, etc.

The form of such pharmaceutical preparations can be selected from various forms according to the purpose of therapy. Typical examples include tablets, pills, powders, solutions, suspensions, emulsions, granules, capsules, suppositories, injections (solutions, suspensions, etc.) and the like.

To form tablets, any of various known carriers can be used, including, for example, lactose, white sugar, sodium chloride, glucose, urea, starch, calcium carbonate, kaolin, crystalline cellulose and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminaran powder, sodium hydrogencarbonate, calcium carbonate, aliphatic acid esters of polyoxyethylenesorbitan, sodium laurylsulfate, stearic acid monoglyceride, starch, lactose and other disintegrants; white sugar, stearin, cacao butter, hydrogenated oils and other disintegration inhibitors; quaternary ammonium base, sodium lauryl sulfate and other absorption promoters; glycerin, starch and other wetting agents; starch, lactose, kaolin, bentonite, colloidal silicic acid and other adsorbents; purified talc, stearates, boric acid powder, polyethylene glycol and other lubricants; etc.

Such tablets may be coated with usual coating materials as required, to prepare, for example, sugar-coated tablets, gelatin-coated tablets, enteric-coated tablets, film-coated tablets, double- or multi-layered tablets, etc.

To form pills, any of various known carriers can be used, including, for example, glucose, lactose, starch, cacao butter, hydrogenated vegetable oils, kaolin, talc and other excipients; gum arabic powder, tragacanth powder, gelatin, ethanol and other binders; laminaran, agar and other disintegrants; etc.

To form suppositories, any of various known carriers can be used, including, for example, polyethylene glycol, cacao butter, higher alcohols, esters of higher alcohols, gelatin, semisynthetic glycerides, etc.

To form an injection, a solution, emulsion or suspension is sterilized and preferably made isotonic with blood. Any of various known widely used diluents can be employed to prepare the solution, emulsion or suspension. Examples of such diluents include water, ethanol, propylene glycol, ethoxylated isostearyl alcohol, polyoxylated isostearyl alcohol, aliphatic acid esters of polyoxyethylene sorbitan, etc. In this case, the pharmaceutical preparation may contain sodium chloride, glucose or glycerin in an amount sufficient to prepare an isotonic solution, and may contain usual solubilizers, buffers, analgesic agents, etc., and further, if necessary, coloring agents, preservatives, flavors, sweetening agents, etc., and/or other medicines.

The proportion of the compound of the present invention in the pharmaceutical preparation is not limited and can be suitably selected from a wide range. It is usually preferable that the pharmaceutical preparation contain the compound of the present invention in a proportion of 1 to 70 wt. %.

The route of administration of the pharmaceutical preparation according to the present invention is not limited, and the preparation can be administered by a route suitable for the form of the preparation, the patient's age and sex, the conditions of the disease, and other conditions. For example, tablets, pills, solutions, suspensions, emulsions, granules and capsules are administered orally. Injections are intravenously administered singly or as mixed with usual injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation is suitably selected according to the method of use, the patient's age and sex, the severity of the disease, and other conditions, and is usually 0.001 to 100 mg/kg body weight/day, and preferably 0.001 to 50 mg/kg body weight/day, in single or divided doses.

Since the dosage varies depending on various conditions, a dosage smaller than the above range may be sufficient, or a dosage larger than the above range may be required.

EXAMPLES

Manufacturing Examples of compounds used in the invention are shown below, being followed by the Pharmacological Test results of these compounds.

Reference Example 1

Production of tert-butyl {3-methoxy-4-[(5-nitropyridin-2-yl)oxy]phenyl}carbamate A mixture of 2-methoxy-4-nitrophenol (3.22 g), di-tert-butyl dicarbonate (4.16 g) and palladium on carbon (5% wt., 2.03 g) in EtOH (100 mL) was stirred at 40° C. for 5 hours under a hydrogen atmosphere. The mixture was filtered through a pad of Celite and the filtrate was concentrated under reduced pressure to give a brown oil. The oil was dissolved in DMF (80 mL). To the solution were added 2-chloro-5-nitropyridine (3.02 g) and potassium carbonate (3.95 g). After stirring at room temperature for 1 hour and 50° C. for 3 hours, the mixture was filtered through a pad of Celite and the filtrate was concentrated under reduced pressure. The residue was diluted in AcOEt and water, and extracted with AcOEt. The organic layer was washed with water, saturated aqueous NaCl, dried over anhydrous $Na_2SO_4$ and concentrated under reduced pressure. To the residue were added $Et_2O$/acetone and the mixture was stirred at room temperature overnight. The resulting precipitate was collected by filtration, and the filtrate was purified by silica gel column chromatography (n-hexane/AcOEt=9/1 to 3/1). These were combined to afford the title compound (5.44 g) as a pale yellow solid.

$^1$H-NMR (CDCl$_3$) δ: 1.53 (9H, s), 3.76 (3H, s), 6.54 (1H, s), 6.76 (1H, dd, J=8.5, 2.4 Hz), 6.99-7.06 (2H, m), 7.43 (1H, s), 8.44 (1H, dd, J=9.0, 2.7 Hz), 9.00-9.02 (1H, m).

Reference Example 2

Production of tert-butyl {3-methyl-4-[(5-nitropyridin-2-yl)oxy]phenyl}carbamate

To a DMF (50 ml) solution of tert-butyl(4-hydroxy-3-methylphenyl)carbamate (5.00 g) was added 2-chloro-5-nitropyridine (3.91 g) and potassium carbonate (4.64 g). After stirring at 80° C. for 4 hours, the mixture was concentrated under reduced pressure. The residue was diluted in AcOEt and water, and extracted with AcOEt. The organic layer was washed with water, saturated aqueous NaCl, dried over anhydrous $Na_2SO_4$ and concentrated under reduced pressure. To the residue were added $Et_2O$ and the mixture was stirred at room temperature for 2 hours. The resulting precipitate was collected by filtration to afford the title compound (6.04 g) as a brown powder.

$^1$H-NMR (CDCl$_3$) δ: 1.52 (9H, s), 2.12 (3H, s), 6.49 (1H, brs), 6.98 (1H, d, J=8.6 Hz), 6.99 (1H, d, J=9.0 Hz), 7.21 (1H, dd, J=8.5, 2.7 Hz), 7.39 (1H, s), 8.46 (1H, dd, J=9.0, 2.9 Hz), 9.03 (1H, d, J=2.9 Hz).

Reference Example 3

Production of tert-butyl {3-methoxy-4-[(5-nitropyridin-2-yl)oxy]phenyl}methylcarbamate To a DMF (80 mL) solution of tert-butyl {3-methoxy-4-[(5-nitropyridin-2-yl)oxy]phenyl}carbamate (4.42 g) was added NaH (60% in oil, 0.51 g) at 0° C. After stirring at 0° C. for 10 min, iodomethane (1.91 g) was added and the mixture was stirred at room temperature for 1 hour. The mixture was poured into ice water and extracted with AcOEt. The organic layer was washed with water, saturated aqueous NaCl and dried over anhydrous $Na_2SO_4$. The solvent was removed under reduced pressure to afford the title compound (4.80 g) as a brown oil.

$^1$H-NMR (CDCl$_3$) δ: 1.49 (9H, s), 3.30 (3H, s), 3.74 (3H, s), 6.87 (1H, dd, J=8.5, 2.4 Hz), 6.96-7.05 (2H, m), 7.09 (1H, d, J=8.5 Hz), 8.45 (1H, dd, J=9.0, 2.7 Hz), 9.02 (1H, d, J=2.4 Hz).

The following compound was produced in the substantially same manner as in Reference Example 3 using appropriate starting materials.

Reference Example 4 tert-Butyl {3-fluoro-4-[5-nitropyridin-2-yl)oxy]phenyl}methylcarbamate $^1$H-NMR (CDCl$_3$) δ: 1.49 (9H, s), 3.30 (3H, s), 7.07-7.24 (4H, m), 8.51 (1H, dd, J=9.0, 2.7 Hz), 9.01 (1H, d, J=2.7 Hz).

Reference Example 5

Production of tert-butyl methyl {3-methyl-4-[(5-nitropyridin-2-yl)oxy]phenyl}carbamate To a DMF (50 mL) suspension of NaH (60% in oil, 640 mg) was added tert-butyl {3-methyl-4-[(5-nitropyridin-2-yl)oxy]phenyl}carbamate (5.00 g) at 0° C. After stirring at 0° C. for 10 min, iodomethane (3.08 g) was added and the mixture was stirred for 3 hour. The mixture was poured into ice water and extracted with AcOEt. The organic layer was washed with water, saturated aqueous NaCl and dried over anhydrous $Na_2SO_4$. The solvent was removed under reduced pressure. The residue was purified by silica gel column chromatography (n-heptane/AcOEt=6/1 to 1/1) to afford the title compound (4.35 g) as a white solid.

$^1$H-NMR (CDCl$_3$) δ: 1.48 (9H, s), 2.14 (3H, s), 3.28 (3H, s), 7.01 (1H, dd, J=9.2, 0.6 Hz), 7.02 (1H, d, J=8.5 Hz), 7.15 (1H, dd, J=8.5, 2.4 Hz), 7.18-7.23 (1H, br m), 8.47 (1H, dd, J=9.2, 2.8 Hz), 9.04 (1H, dd, J=2.7, 0.5 Hz).

Reference Example 6

Production of tert-butyl methyl{4-[(5-nitropyridin-2-yl)oxy]phenyl}carbamate

To a THF (30 mL) suspension of NaH (60% in oil, 1.22 g) was added tert-butyl {4-[(5-nitropyridin-2-yl)oxy]phenyl}carbamate (7.77 g) at 0° C. After stirring at 0° C. for 10 min, iodomethane (4.33 g) was added and the mixture was stirred at room temperature for 3 hours. The mixture was poured into ice water and extracted with AcOEt. The organic layer was washed with water, saturated aqueous NaCl and dried over anhydrous $Na_2SO_4$. The solvent was removed under reduced pressure. The residue was purified by silica gel column chromatography (n-hexane/AcOEt=2/1) to afford the title compound (6.30 g) as a pale yellow solid.

$^1$H-NMR (CDCl$_3$) δ: 1.48 (9H, s), 3.30 (3H, s), 7.03 (1H, dd, J=9.0, 0.5 Hz), 7.11-7.13 (2H, m), 7.31-7.34 (2H, m), 8.48 (1H, dd, J=9.0, 2.7 Hz), 9.05 (1H, d, J=2.7 Hz).

Reference Example 7

Production of tert-butyl {4-[(5-aminopyridin-2-yl)oxy]-3-methoxyphenyl}methylcarbamate A mixture of tert-butyl {3-methoxy-4-[(5-nitropyridin-2-yl)oxy]phenyl}methylcarbamate (4.80 g) and palladium on carbon (5% wt., 1.36 g) in EtOH (100 mL) was stirred at 40° C. for 2 hours under a hydrogen atmosphere. The mixture was filtered through a pad of Celite and the filtrate was concentrated under reduced pressure. The residue was purified by silica gel column chromatography (n-hexane/AcOEt=3/2 to 3/7) to afford the title compound (3.58 g) as a yellow oil.

$^1$H-NMR (CDCl$_3$) δ: 1.46 (9H, s), 3.26 (3H, s), 3.46 (2H, brs), 3.77 (3H, s), 6.73-6.82 (2H, m), 6.88-6.93 (1H, m), 7.00 (1H, d, J=8.3 Hz), 7.07 (1H, dd, J=8.5, 2.9 Hz), 7.66 (1H, d, J=2.9 Hz).

Reference Example 8

Production of tert-butyl {4-[(5-aminopyridin-2-yl)oxy]-3-methylphenyl}methylcarbamate A mixture of tert-butyl methyl {3-methyl-4-[(5-nitropyridin-2-yl)oxy]phenyl}carbamate (4.35 g) and palladium on carbon (10% wt., 620 mg) in AcOEt (80 mL) was stirred at 45° C. for 3 hours under a hydrogen atmosphere. The mixture was filtered through a pad of Celite and the filtrate was concentrated under reduced pressure. The residue was purified by silica gel column chromatography (n-heptane/AcOEt=1/1 to 3/7) to afford the title compound (3.55 g) as a white solid.

$^1$H-NMR (CDCl$_3$) δ: 1.46 (9H, s), 2.19 (3H, s), 3.24 (3H, s), 3.52 (2H, brs), 6.68 (1H, d, J=8.5 Hz), 6.90 (1H, d, J=8.8 Hz), 7.02 (1H, dd, J=8.5, 2.4 Hz), 7.05 (1H, dd, J=8.5, 2.9 Hz), 7.08-7.13 (1H, br m), 7.68 (1H, d, J=2.9 Hz).

Reference Example 9

Production of tert-butyl {4-[(5-aminopyridin-2-yl)oxy]phenyl}methylcarbamate

A mixture of tert-butyl methyl{4-[(5-nitropyridin-2-yl)oxy]phenyl}carbamate (3.28 g) and palladium on carbon (10% wt., 328 mg) in EtOH (30 mL) was stirred at 50° C. for 4 hours under a hydrogen atmosphere. The mixture was filtered through a pad of Celite and the filtrate was concentrated under reduced pressure. The residue was purified by silica gel column chromatography (n-hexane/AcOEt=2/1) to afford the title compound (2.79 g) as a pale yellow solid.

$^1$H-NMR (CDCl$_3$) δ: 1.44 (9H, s), 3.24 (3H, s), 3.54 (2H, brs), 6.76 (1H, d, J=8.5 Hz), 6.99-7.02 (2H, m), 7.08 (1H, dd, J=8.5, 2.9 Hz), 7.17-7.19 (2H, m), 7.72 (1H, d, J=2.9 Hz).

Reference Example 10

Production of tert-butyl {4-[(5-aminopyridin-2-yl)oxy]-3-fluorophenyl}methylcarbamate A solution tert-butyl {3-fluoro-4-[(5-nitropyridin-2-yl)oxy]phenyl}methyl-carbamate (2.79 g) in EtOH (57 mL) was purged with argon then treated with platinum on carbon (5% wt. %, support activated carbon, wet, Degussa type F101 ra/w) (0.6 g). The reaction mixture was then placed under a H$_2$ atmosphere and was vigorously stirred at 40° C. for 2 h. The reaction mixture was filtered through a pad of Celite, the filtrate was concentrated under reduced pressure to afford the title compound as a white powder (2.59 g).

$^1$H-NMR (CDCl$_3$) δ: 1.45 (9H, s), 3.25 (3H, s), 3.48 (2H, brs), 6.82 (1H, d, J=8.7 Hz), 6.98-7.03 (1H, m), 7.07-7.15 (3H, m), 7.64 (1H, dd, J=3.1, 0.6 Hz).

Reference Example 11

Production of tert-butyl [3-fluoro-4-({5-[(4-phenoxybenzoyl)amino]pyridin-2-yl}oxy)phenyl]-methylcarbamate To an AcOEt (12 mL) solution of tert-butyl {4-[(5-aminopyridin-2-yl)oxy]-3-fluorophenyl}methylcarbamate (0.5 g) and triethylamine (0.36 mL) was added a AcOEt (5 mL) solution of 4-phenoxybenzoyl chloride (390 mg) at 0° C., then the resultant mixture was stirred at 0° C. for 10 min. The resulting precipitate was separated and washed with H$_2$O and Et$_2$O to give the title compound as a white powder (0.53 g).

$^1$H-NMR (CDCl$_3$) δ: 1.48 (9H, s), 3.27 (3H, s), 7.01 (1H, d, J=8.8 Hz), 7.03-7.23 (6H, m), 7.05 (2H, d, J=8.8 Hz), 7.36-7.43 (2H, m), 7.77 (1H, s), 7.84 (2H, d, J=8.8 Hz), 8.19 (1H, d, J=2.2 Hz), 8.22 (1H, dd, J=8.7, 2.8 Hz).

The following compounds were produced in the substantially same manner as in Reference Example 11 using appropriate starting materials.

Reference Example 12 tert-Butyl [4-({5-[(biphenyl-4-ylcarbonyl)amino]pyridin-2-yl}oxy)-3-fluorophenyl]methylcarbamate $^1$H-NMR (CDCl$_3$) δ: 1.48 (9H, s), 3.27 (3H, s), 7.03-7.08 (1H, m), 7.03 (1H, d, J=8.8 Hz), 7.14 (1H, d, J=11.7 Hz), 7.17 (1H, t, J=8.7 Hz), 7.38-7.52 (3H, m), 7.61-7.65 (2H, m), 7.72 (2H, d, J=8.5 Hz), 7.87 (1H, s), 7.95 (2H, d, J=8.5 Hz), 8.23 (1H, d, J=2.2 Hz), 8.27 (1H, dd, J=8.7, 2.8 Hz).

Reference Example 13 tert-Butyl {3-fluoro-4-[(5-{[4-(trifluoromethyl)benzoyl]amino}pyridin-2-yl)oxy]phenyl}methylcarbamate $^1$H-NMR (CDCl$_3$) δ: 1.48 (9H, s), 3.26 (3H, s), 6.96-7.18 (4H, m), 7.73 (2H, d, J=8.1 Hz), 7.97 (2H, d, J=8.1 Hz), 8.15 (1H, s), 8.20 (1H, dd, J=8.9, 2.8 Hz), 8.22 (1H, s).

Reference Example 14 tert-Butyl {3-fluoro-4-[(5-{[2-fluoro-4-(trifluoromethyl)benzoyl]amino}pyridin-2-yl)oxy]phenyl}methylcarbamate $^1$H-NMR (CDCl$_3$) δ: 1.48 (9H, s), 3.28 (3H, s), 7.04 (1H, d, J=9.0 Hz), 7.07 (1H, s), 7.14 (1H, d, J=10.0 Hz), 7.18 (1H, t, J=8.7 Hz), 7.49 (1H, d, J=11.7 Hz), 7.61 (1H, d, J=8.3 Hz), 8.21 (1H, dd, J=8.9, 2.8 Hz), 8.27 (1H, d, J=2.7 Hz), 8.28-8.38 (2H, m).

Reference Example 15 tert-Butyl [3-fluoro-4-({5-[(2,3,4-trifluorobenzoyl)amino]pyridin-2-yl]oxy)phenyl}methylcarbamate $^1$H-NMR (CDCl$_3$) δ: 1.48 (9H, s), 3.28 (3H, s), 7.03-7.08 (1H, m), 7.03 (1H, d, J=9.0 Hz), 7.12-7.21 (3H, m), 7.89-7.99 (1H, m), 8.11-8.18 (1H, m), 8.17 (1H, dd, J=8.8, 2.7 Hz), 8.25 (1H, d, J=2.7 Hz).

Reference Example 16 tert-Butyl methyl[3-methyl-4-({5-[(4-phenoxybenzoyl)amino]pyridin-2-yl}oxy)phenyl]carbamate $^1$H-NMR (CDCl$_3$) δ: 1.47 (9H, s), 2.17 (3H, s), 3.26 (3H, s), 6.88 (1H, dd, J=8.8, 0.8 Hz), 6.98 (1H, d, J=8.5 Hz), 7.03-7.09 (5H, m), 7.12-7.16 (1H, br m), 7.18-7.22 (1H, m), 7.37-7.42 (2H, m), 7.84-7.86 (3H, m), 8.18-8.22 (2H, m).

Reference Example 17 tert-Butyl [4-({5-[(biphenyl-4-ylcarbonyl)amino]pyridin-2-yl}oxy)-3-methylphenyl]methylcarbamate $^1$H-NMR (CDCl$_3$) δ: 1.47 (9H, s), 2.17 (3H, s), 3.26 (3H, s), 6.89 (1H, d, J=9.0 Hz), 6.99 (1H, d, J=8.5 Hz), 7.08 (1H, dd, J=8.5, 2.4 Hz), 7.12-7.17 (1H, br m), 7.40-7.42 (1H, m), 7.46-7.50 (2H, m), 7.62-7.64 (2H, m), 7.70-7.72 (2H, m), 7.94-7.97 (2H, m), 7.97-8.00 (1H, br m), 8.22-8.26 (2H, m).

Reference Example 18

Production of tert-butyl methyl{3-methyl-4-[(5-{[4-(trifluoromethyl)benzoyl]amino}pyridin-2-yl)oxy]phenyl}carbamate To an AcOEt (15 mL) solution of tert-butyl {4-[(5-aminopyridin-2-yl)oxy]-3-methylphenyl}methylcarbamate (0.5 g) and Et$_3$N (0.32 mL) was added a 4-(trifluoromethyl)benzoyl chloride (237 mL) slowly at 0° C., then the resultant mixture was stirred at room temperature for 30 min. To the solution was added AcOEt (10 mL) and water (10 mL), the mixture was extracted with AcOEt. The organic layer was washed with saturated aqueous NaHCO$_3$ and saturated aqueous NaCl, dried over anhydrous Na$_2$SO$_4$, and concentrated under reduced pressure. After addition of Hexane (20 mL), the solution was stirred vigorously. The resulting precipitate was collected, affording the title compound (700 mg) as a white solid.

$^1$H-NMR (CDCl$_3$) δ: 1.47 (9H, s), 2.13 (3H, s), 3.24 (3H, s), 6.86 (1H, d, J=8.8 Hz), 6.95 (1H, d, J=8.5 Hz), 7.01-7.08 (1H, m), 7.12 (1H, s), 7.73 (2H, d, J=8.1 Hz), 7.98 (2H, d, J=7.8 Hz), 8.06-8.31 (1H, br m), 8.17 (1H, d, J=8.8 Hz), 8.26 (1H, d, J=2.7 Hz).

The following compounds were produced in the substantially same manner as in Reference Example 18 using appropriate starting materials.

Reference Example 19 tert-Butyl {4-[(5-{[2-fluoro-4-(trifluoromethyl)benzoyl]amino}pyridin-2-yl)oxy]-3-methylphenyl}methylcarbamate $^1$H-NMR (CDCl$_3$) δ: 1.47 (9H, s), 2.18 (3H, s), 3.27 (3H, s), 6.91 (1H, d, J=8.8 Hz), 7.00 (1H, d, J=8.5 Hz), 7.10 (1H, dd, J=8.5, 2.4 Hz), 7.13-7.19 (1H, br m), 7.49 (1H, d, J=11.7 Hz), 7.61 (1H, d, J=8.3 Hz), 8.18 (1H, dd, J=8.8, 2.8 Hz), 8.29-8.36 (3H, m).

Reference Example 20 tert-Butyl methyl[4-({5-[(4-phenoxybenzoyl)amino]pyridin-2-yl}oxy)phenyl]carbamate $^1$H-NMR (CDCl$_3$) δ: 1.46 (9H, s), 3.26 (3H, s), 6.94 (1H, d, J=8.8 Hz), 7.03-7.09 (6H, m), 7.18-7.25 (3H, m), 7.37-7.43 (2H, m), 7.84-7.87 (3H, m), 8.21 (1H, dd, J=8.8, 2.7 Hz), 8.25 (1H, d, J=2.7 Hz).

Reference Example 21 tert-Butyl [4-({5-[(biphenyl-4-ylcarbonyl)amino]pyridin-2-yl}oxy)phenyl]methylcarbamate $^1$H-NMR (CDCl$_3$) δ: 1.46 (9H, s), 3.26 (3H, s), 6.96 (1H, d, J=8.8 Hz), 7.07-7.10 (2H, m), 7.23-7.25 (2H, m), 7.40-7.42 (1H, m), 7.46-7.50 (2H, m), 7.62-7.64 (2H, m), 7.71-7.73 (2H, m), 7.95-7.97 (3H, m), 8.26 (1H, dd, J=8.8, 2.6 Hz), 8.30 (1H, d, J=2.6 Hz).

Example 1

Production of N-{6-[2-fluoro-4-(methylamino)phenoxy]pyridin-3-yl}-4-phenoxybenzamide tert-Butyl [3-fluoro-4-({5-[(4-phenoxybenzoyl)amino]pyridin-2-yl}oxy)phenyl]-methylcarbamate (0.53 g) was dissolved in TFA (4 mL) and stirred at room temperature for 5 min. The mixture was evaporated under reduced pressure and the residue was dissolved in AcOEt. Ice cold 5 M NaOH was added to adjust the pH to 12, and the mixture was extracted with AcOEt. The organic layer was washed with water and saturated aqueous NaCl, dried over anhydrous MgSO$_4$, and concentrated under reduced pressure. The residue was dissolved in Et$_2$O, and the solution was stirred for 1 day. The resulting precipitate was collected and washed with Et$_2$O to give the title compound as a white powder (0.29 g).

$^1$H-NMR (CDCl$_3$) δ: 2.83 (3H, s), 3.78 (1H, brs), 6.35-6.44 (2H, m), 6.96 (1H, d, J=9.3 Hz), 6.99-7.09 (5H, m), 7.17-7.22 (1H, m), 7.36-7.43 (2H, m), 7.68 (1H, s), 7.84 (2H, d, J=8.9 Hz), 8.16-8.23 (2H, m).

The following compounds were produced in the substantially same manner as in Example 1 using appropriate starting materials.

Example 2

N-{6-[2-Fluoro-4-(methylamino)phenoxy]pyridin-3-yl}biphenyl-4-carboxamide mp: 190.0-190.5° C. (dec.)

Example 3

N-{6-[2-Fluoro-4-(methylamino)phenoxy]pyridin-3-yl}-4-(trifluoromethyl)benzamide $^1$H-NMR (CDCl$_3$) δ: 2.82 (3H, s), 6.32-6.46 (2H, m), 6.91-7.06 (2H, m), 7.74 (2H, d, J=8.1 Hz), 7.89 (1H, s), 7.97 (2H, d, J=8.1 Hz), 8.19 (1H, dd, J=8.7, 2.7 Hz), 8.20 (1H, s).

Example 4

2-Fluoro-N-{6-[2-fluoro-4-(methylamino)phenoxy]pyridin-3-yl}-4-(trifluoromethyl)benzamide $^1$H-NMR (CDCl$_3$) δ: 2.83 (3H, d, J=5.1 Hz), 3.80 (1H, d, J=4.9 Hz), 6.36-6.46 (2H, m), 6.98 (1H, d, J=8.8 Hz), 7.03 (1H, t, J=8.7 Hz), 7.49 (1H, d, J=11.7 Hz), 7.60 (1H, d, J=7.3 Hz), 8.17 (1H, dd, J=8.8, 2.7 Hz), 8.26 (1H, d, J=2.4 Hz), 8.27-8.35 (2H, m).

Example 5

2,3,4-Trifluoro-N-{6-[2-fluoro-4-(methylamino)phenoxy]pyridin-3-yl}benzamide $^1$H-NMR (CDCl$_3$) δ: 2.83 (3H, s), 3.81 (1H, brs), 6.35-6.45 (2H, m), 6.97 (1H, d, J=9.0 Hz), 7.03 (1H, t, J=8.7 Hz), 7.10-7.19 (1H, m), 7.88-7.98 (1H, m), 8.12 (1H, brs), 8.13 (1H, dd, J=8.8, 2.7 Hz), 8.24 (1H, d, J=2.7 Hz).

Example 6

N-{6-[2-Methyl-4-(methylamino)phenoxy]pyridin-3-yl}-4-phenoxybenzamide $^1$H-NMR (CDCl$_3$) δ: 2.10 (3H, s), 2.83 (3H, s), 3.63 (1H, brs), 6.47 (1H, dd, J=8.5, 2.7 Hz), -6.50 (1H, d, J=2.4 Hz), 6.82 (1H, d, J=8.8 Hz), 6.89 (1H, d, J=8.5 Hz), 7.03-7.08 (4H, m), 7.17-7.22 (1H, m), 7.38-7.41 (2H, m), 7.79 (1H, brs), 7.83-7.85 (2H, m), 8.15 (1H, dd, J=8.8, 2.8 Hz), 8.18 (1H, d, J=2.4 Hz).

Example 7

N-{6-[2-Methyl-4-(methylamino)phenoxy]pyridin-3-yl}biphenyl-4-carboxamide $^1$H-NMR (CDCl$_3$) δ: 2.11 (3H, s), 2.83 (3H, s), 3.63 (1H, brs), 6.47 (1H, dd, J=8.4, 2.8 Hz), 6.50 (1H, d, J=2.8 Hz), 6.83 (1H, d, J=8.8 Hz), 6.90 (1H, d, J=8.4 Hz), 7.39-7.41 (1H, m), 7.46-7.49 (2H, m), 7.61-7.64 (2H, m), 7.69-7.71 (2H, m), 7.91 (1H, brs), 7.92-7.95 (2H, m), 8.19 (1H, dd, J=8.8, 2.8 Hz), 8.22 (1H, d, J=2.4 Hz).

Example 8

N-{6-[2-Methyl-4-(methylamino)phenoxy]pyridin-3-yl}-4-(trifluoromethyl)benzamide Production of N-{6-[2-methyl-4-(methylamino)phenoxy]pyridin-3-yl}-4-(trifluoromethyl)benzamide To a solution of tert-butyl methyl{3-methyl-4-[(5-{[4-(trifluoromethyl)benzoyl]amino}pyridin-2-yl)oxy]phenyl}carbamate (0.60 g) in CH$_2$Cl$_2$ (1 mL) was added TFA (3.32 mL) in three portion at 0° C. After stirring at 0° C. for 30 min, the mixture was evaporated under reduced pressure and the residue was dissolved in AcOEt. Ice cold 2 M NaOH (10 mL) was added, the mixture was extracted with AcOEt. The organic layer was washed with water and saturated aqueous NaCl, dried over anhydrous Na$_2$SO$_4$, and concentrated under reduced pressure. After addition of Et$_2$O (20 mL), the solution was stirred vigorously. The resulting precipitate was collected and the precipitate was recrystallized from Et2O/AcOEt/Hexane to afford the title compound (0.44 g) as a white powder.

$^1$H-NMR (CDCl$_3$) δ: 2.09 (3H, s), 2.83 (3H, s), 3.64 (1H, s), 6.46 (1H, dd, J=8.5, 2.9 Hz), 6.49 (1H, d, J=2.9 Hz), 6.83 (1H, d, J=9.0 Hz), 6.88 (1H, d, J=8.5 Hz), 7.74 (2H, d, J=8.1 Hz), 7.92-8.01 (3H, m), 8.14 (1H, dd, J=8.9, 2.8 Hz), 8.21 (1H, d, J=2.7 Hz).

The following compounds were produced in the substantially same manner as in Example 8 using appropriate starting materials.

Example 9

2-Fluoro-N-{6-[2-methyl-4-(methylamino)phenoxy]pyridin-3-yl}-4-(trifluoromethyl)benzamide $^1$H-NMR (CDCl$_3$) δ: 2.11 (3H, s), 2.84 (3H, s), 3.65 (1H, brs), 6.48 (1H, dd, J=8.4, 2.8 Hz), 6.51 (1H, d, J=2.4 Hz), 6.84 (1H, d, J=8.8 Hz), 6.90 (1H, d, J=8.4 Hz), 7.48 (1H, d, J=11.7 Hz), 7.60 (1H, d, J=8.1 Hz), 8.13 (1H, dd, J=8.8, 2.8 Hz), 8.27-8.34 (3H m).

Example 10

N-{6-[4-(Methylamino)phenoxy]pyridin-3-yl}-4-phenoxybenzamide $^1$H-NMR (CDCl$_3$) δ: 2.84 (3H, s), 6.61-6.64 (2H, m), 6.86 (1H, d, J=8.8 Hz), 6.96-6.99 (2H, m), 7.03-7.07 (4H, m), 7.18-7.21 (1H, m), 7.38-7.41 (2H, m), 7.80 (1H, brs), 7.83-7.85 (2H, m), 8.15 (1H, dd, J=8.8, 2.8 Hz), 8.20 (1H, d, J=2.8 Hz).

Example 11

N-{6-[4-(Methylamino)phenoxy]pyridin-3-yl}biphenyl-4-carboxamide $^1$H-NMR (CDCl$_3$) δ: 2.84 (3H, s), 6.62-6.64 (2H, m), 6.87 (1H, d, J=8.8 Hz), 6.98-6.99 (2H, m), 7.40-7.41 (1H, m), 7.46-7.49 (2H, m), 7.61-7.64 (2H, m), 7.69-7.71 (2H, m), 7.90 (1H, brs), 7.93-7.95 (2H, m), 8.19 (1H, dd, J=8.8, 2.6 Hz), 8.24 (1H, d, J=2.6 Hz).

Example 12

Production of N-{6-[2-methoxy-4-(methylamino)phenoxy]pyridin-3-yl}-4-(trifluoromethyl)benzamide To an AcOEt (10 mL) solution of tert-butyl {4-[(5-aminopyridin-2-yl)oxy]-3-methoxyphenyl}methylcarbamate (0.60 g) and triethylamine (0.26 g) was added 4-(trifluoromethyl)benzoyl chloride (0.38 g) at 0° C. The mixture was stirred at room temperature for 1 hour. The mixture was poured into water and extracted with AcOEt. The organic layer was washed with water, saturated aqueous NaCl, dried over anhydrous Na$_2$SO$_4$ and concentrated under reduced pressure. The residue was purified by column chromatography (n-hexane/AcOEt=9/1 to 7/3) to give a yellow amorphous powder. The powder was dissolved in CH$_2$Cl$_2$ (10 mL), then added TFA (1 mL). The mixture was stirred at room temperature for 2 hours. After removal of the solvent under reduced pressure, the residue was poured into saturated aqueous NaHCO$_3$ and extracted with AcOEt. The organic layer was washed with water, saturated aqueous NaCl, dried over anhydrous Na$_2$SO$_4$ and concentrated under reduced pressure. The residue was purified by silica gel column chromatography (n-hexane/AcOEt=7/3 to 3/7) to afford the title compound (0.42 g) as a colorless oil.

$^1$H-NMR (CDCl$_3$) δ: 2.84 (3H, s), 3.73 (3H, s), 6.20 (1H, dd, J=8.5, 2.7 Hz), 6.25 (1H, d, J=2.7 Hz), 6.89 (1H, d, J=8.8 Hz), 6.95 (1H, d, J=8.3 Hz), 7.74 (2H, d, J=8.3 Hz), 7.94-8.02 (3H, m), 8.11-8.22 (2H, m).

The following compounds were produced in the substantially same manner as in Example 12 using appropriate starting materials.

Example 13

N-{6-[2-Methoxy-4-(methylamino)phenoxy]pyridin-3-yl}-4-phenoxybenzamide $^1$H-NMR (CDCl$_3$) δ: 2.84 (3H, s), 3.73 (3H, s), 3.74 (1H, s), 6.18-6.27 (2H, m), 6.88 (1H, d, J=8.8 Hz), 6.94-6.98 (1H, m), 7.01-7.09 (4H, m), 7.17-7.22 (1H, m), 7.36-7.43 (2H, m), 7.72-7.87 (3H, m), 8.11-8.18 (2H, m).

Example 14

N-{6-[2-Methoxy-4-(methylamino)phenoxy]pyridin-3-yl}biphenyl-4-carboxamide mp: 161.4-161.8° C.

Example 15

2-Fluoro-N-{6-[2-methoxy-4-(methylamino)phenoxy]pyridin-3-yl}-4-(trifluoromethyl)benzamide $^1$H-NMR (CDCl$_3$) δ: 2.86 (3H, s), 3.65-3.85 (1H, brm), 3.75 (3H, s), 6.22 (1H, dd, J=8.5, 2.7 Hz), 6.28 (1H, d, J=2.4 Hz), 6.90 (1H, d, J=8.8 Hz), 6.97 (1H, d, J=8.5 Hz), 7.48 (1H, d, J=11.7 Hz), 7.60 (1H, d, J=8.1 Hz), 8.12 (1H, dd, J=8.8, 2.7 Hz), 8.24-8.35 (3H, m).

Example 16

2,3,4-Trifluoro-N-{6-[2-methoxy-4-(methylamino)phenoxy]pyridin-3-yl}benzamide $^1$H-NMR (CDCl$_3$) δ: 2.86 (3H, s), 3.68-3.78 (4H, m), 6.22 (1H, dd, J=8.5, 2.7 Hz), 6.27 (1H, d, J=2.4 Hz), 6.90 (1H, d, J=8.8 Hz), 6.97 (1H, d, J=8.5 Hz), 7.10-7.19 (1H, m), 7.89-7.97 (1H, m), 8.06-8.16 (2H, m), 8.24 (1H, d, J=2.7 Hz).

Example 17

2,3,4-Trifluoro-N-{6-[2-methyl-4-(methylamino)phenoxy]pyridin-3-yl}benzamide $^1$H-NMR (CDCl$_3$) δ: 2.11 (3H, s), 2.83 (3H, s), 3.57-3.72 (1H, m), 6.48 (1H, dd, J=8.5, 2.9 Hz), 6.51 (1H, d, J=2.9 Hz), 6.83 (1H, d, J=8.8 Hz), 6.90 (1H, d, J=8.5 Hz), 7.10-7.19 (1H, m), 7.87-7.96 (1H, m), 8.07-8.12 (1H, m), 8.12-8.21 (1H, m), 8.23-8.28 (1H, m).

Example 18

N-{6-[4-(Methylamino)phenoxy]pyridin-3-yl}-4-(trifluoromethyl)benzamide $^1$H-NMR (CDCl$_3$) δ: 2.84 (3H, s), 6.61-6.63 (2H, m), 6.87 (1H, d, J=8.8 Hz), 6.94-6.97 (2H, m), 7.73-7.75 (2H, m), 7.97-7.99 (2H, m), 8.04 (1H, brs), 8.14 (1H, dd, J=8.8, 2.6 Hz), 8.23 (1H, d, J=2.6 Hz).

Example 19

2-Fluoro-N-{6-[4-(methylamino)phenoxy]pyridin-3-yl}-4-(trifluoromethyl)benzamide $^1$H-NMR (CDCl$_3$) δ: 2.85 (3H, s), 3.70 (1H, brs), 6.63-6.65 (2H, m), 6.88 (1H, d, J=8.8 Hz), 6.98-7.00 (2H, m), 7.49 (1H, d, J=12.0 Hz), 7.60 (1H, dd, J=8.3, 1.0 Hz), 8.14 (1H, dd, J=8.8, 2.8 Hz), 8.28-8.34 (3H, m).

Example 20

2,3,4-Trifluoro-N-{6-[4-(methylamino)phenoxy]pyridin-3-yl}benzamide

Production of 2,3,4-trifluoro-N-{6-[4-(methylamino)phenoxy]pyridin-3-yl}benzamide To an AcOEt (10 mL) solution of tert-butyl {4-[(5-aminopyridin-2-yl)oxy]phenyl}methylcarbamate (0.50 g) and triethylamine (0.32 g) was added 2,3,4-trifluorobenzoyl chloride (0.37 g) at 0° C. The mixture was stirred at room temperature for 1 hour. The mixture was poured into water and extracted with AcOEt. The organic layer was washed with water, saturated aqueous NaCl, dried over anhydrous Na$_2$SO$_4$ and concentrated under reduced pressure. The residue was dissolved in CH$_2$Cl$_2$ (10 mL), then added TFA (3 mL). After stirring at room temperature for 2 hours, the mixture was poured into saturated aqueous NaHCO$_3$ and extracted with AcOEt. The organic layer was washed with water, saturated aqueous NaCl, dried over anhydrous Na$_2$SO$_4$ and concentrated under reduced pressure. The residue was purified by silica gel column chromatography (n-hexane/AcOEt=2/1) to afford the title compound (0.55 g) as a white solid.

$^1$H-NMR (CDCl$_3$) δ: 2.84 (3H, s), 3.71 (1H, brs), 6.62-6.65 (2H, m), 6.87 (1H, d, J=8.8 Hz), 6.97-6.99 (2H, m), 7.11-7.18 (1H, m), 7.89-7.95 (1H, m), 8.10 (1H, dd, J=8.8, 2.7 Hz), 8.14-8.17 (1H, br m), 8.27 (1H, d, J=2.7 Hz).

Example 21

Production of N-{6-[2-fluoro-4-(methylamino)phenoxy]pyridin-3-yl}-4-phenoxybenzamide hydrochloride To an EtOH (7 mL) solution of N-{6-[2-fluoro-4-(methylamino)phenoxy]pyridin-3-yl}-4-phenoxybenzamide (0.34 g) was added 6 M HCl (0.14 mL) at 0° C. The resultant mixture was stirred at 0° C. The resulting precipitate was recrystallized from EtOH/H$_2$O to give the title compound as a white powder (0.28 g).

$^1$H-NMR (DMSO-d$_6$) δ: 2.76 (3H, s), 6.60-6.69 (1H, m), 6.70-6.80 (1H, m), 7.06 (1H, d, J=8.8 Hz), 7.08-7.17 (5H, m), 7.20-7.26 (1H, m), 7.43-7.49 (2H, m), 8.01 (2H, d, J=9.4 Hz), 8.18 (1H, dd, J=8.8, 2.7 Hz), 8.41 (1H, d, J=2.2 Hz), 10.35 (1H, s).

The following compounds were produced in the substantially same manner as in Example 21 using appropriate starting materials.

Example 22

2-Fluoro-N-{6-[2-fluoro-4-(methylamino)phenoxy]pyridin-3-yl}-4-(trifluoromethyl)benzamide hydrochloride $^1$H-NMR (DMSO-d$_6$) δ: 2.77 (3H, s), 6.66-6.76 (1H, m), 6.77-6.88 (1H, m), 7.10 (1H, d, J=9.0 Hz), 7.17 (1H, t, J=8.9 Hz), 7.75 (1H, d, J=8.3 Hz), 7.87-7.95 (2H, m), 8.17 (1H, dd, J=9.0, 2.7 Hz), 8.38 (1H, d, J=2.4 Hz), 10.78 (1H, s).

Example 23

2,3,4-Trifluoro-N-{6-[2-fluoro-4-(methylamino)phenoxy]pyridin-3-yl}benzamide hydrochloride $^1$H-NMR (DMSO-d$_6$) δ: 2.78 (3H, s), 6.70-6.81 (1H, m), 6.82-6.94 (1H, m), 7.10 (1H, d, J=9.0 Hz), 7.19 (1H, t, J=8.8 Hz), 7.44-7.54 (1H, m), 7.56-7.65 (1H, m), 8.16 (1H, dd, J=8.8, 2.7 Hz), 8.37 (1H, d, J=2.4 Hz), 10.70 (1H, s).

Example 24

Production of N-{6-[2-methyl-4-(methylamino)phenoxy]pyridin-3-yl}-4-(trifluoromethyl)benzamide hydrochloride To an EtOH (3 mL) solution of N-{6-[2-Methyl-4-(methylamino)phenoxy]pyridin-3-yl}-4-(trifluoromethyl)benzamide (0.30 g) was added 6 M aqueous HCl (0.13 mL) at 0° C. The resultant mixture was stirred at 0° C. The resulting precipitate was recrystallized from EtOH/H$_2$O, giving the title compound as a white powder (0.20 g).

$^1$H-NMR (DMSO-d$_6$) δ: 2.14 (3H, s), 2.91 (3H, s), 7.11 (1H, d, J=9.0 Hz), 7.17 (1H, d, J=8.5 Hz), 7.32 (1H, dd, J=8.5, 2.4 Hz), 7.36-7.43 (1H, m), 7.93 (2H, d, J=8.3 Hz), 8.19 (2H, d, J=8.1 Hz), 8.25 (1H, dd, J=8.9, 2.8 Hz), 8.48 (1H, d, J=2.4 Hz), 10.71 (1H, s).

The following compounds were produced in the substantially same manner as in Example 24 using appropriate starting materials.

Example 25

2,3,4-Trifluoro-N-{6-[2-methyl-4-(methylamino)phenoxy]pyridin-3-yl}benzamide hydrochloride mp: 222.9-225.4° C. (dec.)

Example 26

N-{6-[2-Methoxy-4-(methylamino)phenoxy]pyridin-3-yl}-4-phenoxybenzamide hydrochloride mp: 202.2-202.3° C.

Example 27

N-{6-[2-Methoxy-4-(methylamino)phenoxy]pyridin-3-yl}-4-(trifluoromethyl)benzamide hydrochloride mp: 217.6-218.2° C.

Example 28

2-Fluoro-N-{6-[2-methoxy-4-(methylamino)phenoxy]pyridin-3-yl}-4-(trifluoromethyl)benzamide hydrochloride mp: 197.0-198.1° C.

Example 29

2,3,4-Trifluoro-N-{6-[2-methoxy-4-(methylamino)phenoxy]pyridin-3-yl}benzamide hydrochloride mp: 207.1-209.8° C.

Example 30

N-{6-[4-(Methylamino)phenoxy]pyridin-3-yl}-4-(trifluoromethyl)benzamide hydrochloride $^1$H-NMR (DMSO-$d_6$) δ: 2.90 (3H, s), 7.12 (1H, d, J=8.8 Hz), 7.23-7.24 (2H, m), 7.42-7.44 (2H, m), 7.92-7.94 (2H, m), 8.18-8.20 (2H, m), 8.26 (1H, dd, J=8.8, 2.6 Hz), 8.54 (1H, d, J=2.6 Hz), 10.73 (1H, s).

Example 31

2-Fluoro-N-{6-[4-(methylamino)phenoxy]pyridin-3-yl}-4-(trifluoromethyl)benzamide hydrochloride $^1$H-NMR (DMSO-$d_6$) δ: 2.89 (3H, s), 7.11 (1H, d, J=8.8 Hz), 7.20-7.22 (2H, m), 7.37-7.39 (2H, m), 7.75 (1H, d, J=8.1 Hz), 7.90-7.94 (2H, m), 8.20 (1H, dd, J=8.8, 2.6 Hz), 8.46 (1H, d, J=2.6 Hz), 10.83 (1H, s).

Example 32

Production of 2,3,4-trifluoro-N-{6-[4-(methylamino)phenoxy]pyridin-3-yl}benzamide hydrochloride (1:1)

To an EtOH (10 mL) solution of 2,3,4-trifluoro-N-{6-[4-(methylamino)phenoxy]pyridin-3-yl}benzamide (0.55 g) was added 6 M HCl (0.27 mL) at room temperature. The resultant mixture was stirred at room temperature. The resulting precipitate was collected by filtration to give the title compound as a white powder (0.35 g).

$^1$H-NMR (DMSO-$d_6$) δ: 2.89 (3H, s), 7.11 (1H, d, J=8.8 Hz), 7.20-7.23 (2H, m), 7.38-7.40 (2H, m), 7.47-7.52 (1H, m), 7.58-7.64 (1H, m), 8.18 (1H, dd, J=8.8, 2.7 Hz), 8.45 (1H, d, J=2.7 Hz), 10.75 (1H, s).

The following compounds can be produced in the substantially same manner as in Example 21 using appropriate starting materials.

Example 33

N-{6-[2-Fluoro-4-(methylamino)phenoxy]pyridin-3-yl}biphenyl-4-carboxamide hydrochloride

Example 34

N-{6-[2-Fluoro-4-(methylamino)phenoxy]pyridin-3-yl}-4-(trifluoromethyl)benzamide hydrochloride

Example 35

N-{6-[2-Methyl-4-(methylamino)phenoxy]pyridin-3-yl}-4-phenoxybenzamide hydrochloride

Example 36

N-{6-[2-Methyl-4-(methylamino)phenoxy]pyridin-3-yl}biphenyl-4-carboxamide hydrochloride

Example 37

2-Fluoro-N-{6-[2-methyl-4-(methylamino)phenoxy]pyridin-3-yl}-4-(trifluoromethyl)benzamide hydrochloride

Example 38

N-{6-[4-(Methylamino)phenoxy]pyridin-3-yl}-4-phenoxybenzamide hydrochloride

Example 39

N-{6-[4-(Methylamino)phenoxy]pyridin-3-yl}biphenyl-4-carboxamide hydrochloride

Example 40

N-{6-[2-Methoxy-4-(methylamino)phenoxy]pyridin-3-yl}biphenyl-4-carboxamide hydrochloride Pharmacological Test
Antiproliferative Effect on Cancer Cells (In Vitro)

Growth inhibition of human hepatic cancer cells (HuH-7) was determined by the sulforhodamine B method based on the method of Skehan P. et al. (J Natl Cancer Inst. 1990 Jul. 4; 82(13): 1107-12). In the study, HuH-7 cells were seeded on DMEM medium containing 10% fetal bovine serum in a 96-well microplate. After 24-hour incubation at 37° C. in the presence of 5% carbon dioxide, the test compound was added and the cells were incubated for another 5 days. After incubation, a trichloroacetic acid solution was added to yield the final concentration of 10% and the cells were left to stand at 4° C. for 1 hour to fix. Then, the cells were washed with water to remove the medium and trichloroacetic acid and dried in the air. The dried cells were stored at 4° C. until they were stained with sulforhodamine B. To each well, 1% acetic acid solution containing 0.4% sulforhodamine B was added and left to stand for 20 to 30 minutes at room temperature. After discarding the supernatant, each well was washed with 1% acetic acid solution, and 10 mM Tris(tris-(hydroxymethyl) aminomethane) solution was added while stirring to elute the dye taken into the cells. Then, the optical density was determined at the measurement wavelength of 492 nm and the reference wavelength of 690 nm, and the difference was calculated. The cell growth activity in each well was defined as the value determined by subtracting the OD in the control well not containing cells (the difference in absorbance between 492 nm and 690 nm) from that in the test well.

The 50% inhibitory concentration ($IC_{50}$ (nM)) of the test compound was determined by comparing the cell growth activity in the well containing the test compound with that of the control not containing the test compound.

The results are shown in Table 2.

TABLE 2

| Test compound | $IC_{50}$(nM) |
|---|---|
| Compound of Example 2 | 108.0 |
| Compound of Example 3 | 154.8 |
| Compound of Example 6 | 78.5 |
| Compound of Example 7 | 77.6 |
| Compound of Example 9 | 70.4 |
| Compound of Example 10 | 319.7 |
| Compound of Example 11 | 310.9 |
| Compound of Example 14 | 247.6 |
| Compound of Example 21 | 136.0 |
| Compound of Example 22 | 162.7 |
| Compound of Example 23 | 752.6 |
| Compound of Example 24 | 72.3 |
| Compound of Example 25 | 484.7 |
| Compound of Example 26 | 274.9 |
| Compound of Example 27 | 303.8 |
| Compound of Example 28 | 292.9 |
| Compound of Example 30 | 274.7 |
| Compound of Example 31 | 327.0 |

Metabolic Stability Test in Hepatic Microsome

In this study, 222.5 µL of 0.22 mg/mL liver microsome was distributed to each tube, and 2.5 µL of 100 µM test compound was added thereto. Then, 22.5 µL of this mixture was divided to 500 µL of acetonitrile spiked IS as 0 min sample, and the residue was pre-incubated at 37° C. for 5 min. Reaction was started by the addition of 22.5 µL of 10 mM NADH/NADPH, and after 10 and 20 min, 25 µL of the reaction mixture was divided to 500 µL of acetonitrile spiked IS. The samples were centrifuged (5700 rpm, 4° C., 10 min), and the supernatants were analyzed by LC/MS/MS. The slope of the linear regression from log percentage remaining versus incubation time relationships ($-k_e$) was calculated, and the intrinsic clearance ($CL_{int}$) was calculated using the following equation.

$$CL_{int} = k_e * \frac{\mu L \text{ incubation}}{\text{mg microsomes}} * \frac{\text{mg microsomes/g liver}}{\text{g liver/kg body weight}}$$

The results are shown in Table 3.

TABLE 3

| Test compound | CLint[µL/min/mg] |
|---|---|
| Compound of Example 2 | <200 |
| Compound of Example 3 | <200 |
| Compound of Example 6 | <200 |
| Compound of Example 7 | <200 |

TABLE 3-continued

| Test compound | CLint[µL/min/mg] |
|---|---|
| Compound of Example 9 | <200 |
| Compound of Example 14 | <200 |
| Compound of Example 22 | <200 |
| Compound of Example 24 | <200 |
| Compound of Example 25 | <200 |
| Compound of Example 26 | <200 |
| Compound of Example 27 | <200 |
| Compound of Example 28 | <200 |
| Compound of Example 30 | <200 |
| Compound of Example 31 | <200 |

Stability Test

In order to estimate the stability of compounds without conducting a long-term stability test, the stability of the dissolved compounds was evaluated under a heat- and acid-stress condition.

About 0.005 g of test compound was dissolved in 50 mL of a mobile phase, and this solution was used as the sample solution. The solutions were put into a brown glass vial and stored at 70° C. during the test period. The test with 20 µL of each of the sample solution was conducted at the following sampling points as directed under the Liquid Chromatography according to the following conditions. The residual ratio of the test compound's peak area (%) in the total peak area detected in the solution was determined by the automatic integration method. Operating conditions were as follows. Detector: An ultraviolet absorption photometer (wavelength: 254 nm); Column: A stainless steel column about 4 mm in inside diameter and about 15 cm in length, packed with octadecylsilanized silica gel for liquid chromatography (5 um in particle diameter).; Column temperature: A constant temperature of about 40° C.; Mobile phase: A mixture of water, acetonitrile and trifluoroacetic acid (500:500:1); Flow rate: 1 mL/min.; Measurement time: 25 minutes; Sampling points: Day 0, Day 1 and Day 3. The residual ratio of the test compound's peak area (%) is calculated as follows. The peak area of the test compound/The total peak area detected in the solution×100.

By the above method, it was confirmed that some representative compounds such as Example 30 possess superior storage stability.

The invention claimed is:

1. A compound represented by the following general formula (1) or a salt thereof:

[Formula 1]

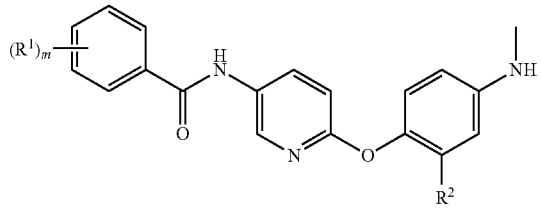

(1)

wherein $R^1$ represents a halogen atom which is not chlorine, an aryl group, an aryloxy group or a linear or branched alkyl group having 1 to 6 carbon atoms, said alkyl group being optionally substituted with one or more halogen atoms;

R² represents a hydrogen atom, a halogen atom, a linear or branched alkyl group having 1 to 6 carbon atoms or a linear or branched alkoxy group having 1 to 6 carbon atoms; and;

m represents an integer of 1 to 3;

provided that when m represents 2 or 3, R¹s are the same or different.

2. The compound according to claim 1 or a salt thereof, wherein R² represents a hydrogen atom.

3. The compound according to claim 1 or a salt thereof, wherein R² represents a halogen atom.

4. The compound according to claim 1 or a salt thereof, wherein R² represents a linear or branched alkyl group having 1 to 6 carbon atoms.

5. The compound according to claim 1 or a salt thereof, wherein R² represents a linear or branched alkoxy group having 1 to 6 carbon atoms.

6. A compound or a salt thereof, which is selected from the group consisting of:
N-{6-[2-fluoro-4-(methylamino)phenoxy]pyridin-3-yl}-4-phenoxybenzamide,
N-{6-[2-fluoro-4-(methylamino)phenoxy]pyridin-3-yl}biphenyl-4-carboxamide,
N-{6-[2-fluoro-4-(methylamino)phenoxy]pyridin-3-yl}-4-(trifluoromethyl)benzamide,
2-fluoro-N-{6-[2-fluoro-4-(methylamino)phenoxy]pyridin-3-yl}-4-(trifluoromethyl)benzamide,
2,3,4-trifluoro-N-{6-[2-fluoro-4-(methylamino)phenoxy]pyridin-3-yl}benzamide,
N-{6-[2-methyl-4-(methylamino)phenoxy]pyridin-3-yl}-4-phenoxybenzamide,
N-{6-[2-methyl-4-(methylamino)phenoxy]pyridin-3-yl}biphenyl-4-carboxamide,
N-{6-[2-methyl-4-(methylamino)phenoxy]pyridin-3-yl}-4-(trifluoromethyl)benzamide,
2-fluoro-N-{6-[2-methyl-4-(methylamino)phenoxy]pyridin-3-yl}-4-(trifluoromethyl)benzam id,
N-{6-[4-(methylamino)phenoxy]pyridin-3-yl}-4-phenoxybenzamide],
N-{6-[4-(methylamino)phenoxy]pyridin-3-yl}biphenyl-4-carboxamide,
N-{6-[2-methoxy-4-(methylamino)phenoxy]pyridin-3-yl}-4-(trifluoromethyl)benzamide,
N-{6-[2-methoxy-4-(methylamino)phenoxy]pyridin-3-yl}-4-phenoxybenzamide,
N-{6-[2-methoxy-4-(methylamino)phenoxy]pyridin-3-yl}biphenyl-4-carboxamide,
2-fluoro-N-{6-[2-methoxy-4-(methylamino)phenoxy]pyridin-3-yl}-4-(trifluoromethyl)benzamide,
2,3,4-trifluoro-N-{6-[2-methoxy-4-(methylamino)phenoxy]pyridin-3-yl}benzamide,
2,3,4-trifluoro-N-{6-[2-methyl-4-(methylamino)phenoxy]pyridin-3-yl}benzamide,
N-{6-[4-(methylamino)phenoxy]pyridin-3-yl}-4-(trifluoromethyl)benzamide,
2-fluoro-N-{6-[4-(methylamino)phenoxy]pyridin-3-yl}-4-(trifluoromethyl)benzamide, and
2,3,4-trifluoro-N-{6-[4-(methylamino)phenoxy]pyridin-3-yl}benzamide.

7. A compound selected from the group consisting of:
N-{6-[2-fluoro-4-(methylamino)phenoxy]pyridin-3-yl}-4-phenoxybenzamide,
N-{6-[2-fluoro-4-(methylamino)phenoxy]pyridin-3-yl}biphenyl-4-carboxamide,
N-{6-[2-fluoro-4-(methylamino)phenoxy]pyridin-3-yl}-4-(trifluoromethyl)benzamide,
2-fluoro-N-{6-[2-fluoro-4-(methylamino)phenoxy]pyridin-3-yl}-4-(trifluoromethyl)benzamide,
2,3,4-trifluoro-N-{6-[2-fluoro-4-(methylamino)phenoxy]pyridin-3-yl}benzamide,
N-{6-[2-methyl-4-(methylamino)phenoxy]pyridin-3-yl}-4-phenoxybenzamide,
N-{6-[2-methyl-4-(methylamino)phenoxy]pyridin-3-yl}biphenyl-4-carboxamide,
N-{6-[2-methyl-4-(methylamino)phenoxy]pyridin-yl}-4-(trifluoromethyl)benzamide,
2-fluoro-N-{6-[2-methyl-4-(methylamino)phenoxy]pyridin-3-yl}-4-(trifluoromethyl)benzamide,
N-{6-[4-(methylamino)phenoxy]pyridin-3-yl}-4-phenoxybenzamide,
N-{6-[4-(methylamino)phenoxy]pyridin-3-yl}biphenyl-4-carboxamide,
N-{6-[2-methoxy-4-(methylamino)phenoxy]pyridin-3-yl}-4-(trifluoromethyl)benzamide,
N-{6-[2-methoxy-4-(methylamino)phenoxy]pyridin-3-yl}-4-phenoxybenzamide,
N-{6-[2-methoxy-4-(methylamino)phenoxy]pyridin-3-yl}biphenyl-4-carboxamide,
2-fluoro-N-{6-[2-methoxy-4-(methylamino)phenoxy]pyridin-3-yl}-4-(trifluoromethyl)benzamide,
2,3,4-trifluoro-N-{6-[2-methoxy-4-(methylamino)phenoxy]pyridin-3-yl}benzamide,
2,3,4-trifluoro-N-{6-[2-methyl-4-(methylamino)phenoxy]pyridin-3-yl}benzamide,
N-{6-[4-(methylamino)phenoxy]pyridin-3-yl}-4-(trifluoromethyl)benzamide,
2-fluoro-N-{6-[4-(methylamino)phenoxy]pyridin-3-yl}4-(trifluoromethyl)benzamide,
2,3,4-trifluoro-N-{6-[4-(methylamino)phenoxy]pyridin-3-yl}benzamide,
N-{6-[2-fluoro-4-(methylamino)phenoxy]pyridin-3-yl}-4-phenoxybenzamide hydrochloride,
2-fluoro-N-{6-[2-fluoro-4-(methylamino)phenoxy]pyridin-3-yl}-4-(trifluoromethyl)benzamide hydrochloride,
2,3,4-trifluoro-N-{6-[2-fluoro-4-(methylamino)phenoxy]pyridin-3-yl}benzamide hydrochloride,
N-{6-[2-methyl-4-(methylamino)phenoxy]pyridin-3-yl}-4-(trifluoromethyl)benzamide hydrochloride,
2,3,4-trifluoro-N-{6-[2-methyl-4-(methylamino)phenoxy]pyridin-3-yl}benzamide hydrochloride,
N-{6-[2-methoxy-4-(methylamino)phenoxy]pyridin-3-yl}-4-phenoxybenzamide hydrochloride,
N-{6-[2-methoxy-4-(methylamino)phenoxy]pyridin-3-yl}-4-(trifluoromethyl)benzamide hydrochloride,
2-fluoro-N-{6-[2-methoxy--4-(methylamino)phenoxy]pyridin-3-yl}-4-(trifluoromethyl)benzamide hydrochloride,
2,3,4-trifluoro-N-{6-[2-methoxy-4-(methylamino)phenoxy]pyridin-3-yl}benzamide hydrochloride,
N-{6-[4-(methylamino)phenoxy]pyridin-3-yl}-4-(trifluoromethyl)benzamide hydrochloride,
2-fluoro-N-{6-[4-(methylamino)phenoxy]pyridin-3-yl}-4-(trifluoromethyl)benzamide hydrochloride, and
2,3,4-trifluoro-N-{6-[4-(methylamino)phenoxy]pyridin-3-yl}benzamide hydrochloride.

8. A pharmaceutical composition comprising a compound represented by the general formula (1) or a salt thereof according to claim 1, and a pharmacologically acceptable carrier.

* * * * *

UNITED STATES PATENT AND TRADEMARK OFFICE
CERTIFICATE OF CORRECTION

PATENT NO. : 8,946,437 B2  
APPLICATION NO. : 13/877276  
DATED : February 3, 2015  
INVENTOR(S) : Takashi Nakagawa et al.

It is certified that error appears in the above-identified patent and that said Letters Patent is hereby corrected as shown below:

Title Page

(54) Title, Col. 1, Line 1, "Benzamide" is printed overlapping the first column of Col. 2.

In the Specification

Col. 1, Line 1, "4-(METHYLAMINOPHENOXY)PYRDIN-3-YL-BENZAMIDE" should read as --4-(METHYLAMINOPHENOXY)PYRIDIN-3-YL-BENZAMIDE--.

In the Claims

Claim 6, Col. 29, Lines 36-37, "2-fluoro-N-[6-[2-methyl-4-(methylamino)phenoxy]pyridin-3-yl}-4-(trifluoromethyl)benzam id," should read as --2-fluoro-N-[6-[2-methyl-4-(methylamino)phenoxy]pyridin-3-yl}-4-(trifluoromethyl)benzamide--.

Signed and Sealed this  
Ninth Day of June, 2015

Michelle K. Lee  
*Director of the United States Patent and Trademark Office*